(12) United States Patent
Atwood et al.

(10) Patent No.: US 9,597,369 B2
(45) Date of Patent: *Mar. 21, 2017

(54) INHIBITORS OF ATYPICAL PROTEIN KINASE C AND THEIR USE IN TREATING HEDGEHOG PATHWAY-DEPENDENT CANCERS

(71) Applicant: The Board of Trustees of the Leland Stanford Junior University, Stanford, CA (US)

(72) Inventors: Scott X. Atwood, Stanford, CA (US); Anthony Oro, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,916

(22) Filed: Jun. 2, 2015

(65) Prior Publication Data

US 2015/0335702 A1 Nov. 26, 2015

Related U.S. Application Data

(63) Continuation of application No. 13/422,936, filed on Mar. 16, 2012, now Pat. No. 9,073,964.

(60) Provisional application No. 61/483,393, filed on May 6, 2011.

(51) Int. Cl.
| | |
|---|---|
| *A61K 31/713* | (2006.01) |
| *A61K 38/10* | (2006.01) |
| *G01N 33/574* | (2006.01) |
| *C07K 7/06* | (2006.01) |
| *C07K 7/08* | (2006.01) |
| *C07D 403/12* | (2006.01) |
| *C07D 491/107* | (2006.01) |
| *C07D 211/40* | (2006.01) |
| *C12N 15/113* | (2010.01) |

(52) U.S. Cl.
CPC ............ *A61K 38/10* (2013.01); *A61K 31/713* (2013.01); *C07D 211/40* (2013.01); *C07D 403/12* (2013.01); *C07D 491/107* (2013.01); *C07K 7/06* (2013.01); *C07K 7/08* (2013.01); *C12N 15/1137* (2013.01); *C12Y 207/11013* (2013.01); *G01N 33/5743* (2013.01); *C12N 2310/14* (2013.01); *C12N 2310/531* (2013.01); *G01N 2333/912* (2013.01); *G01N 2440/14* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 2006/0185026 A1 | 8/2006 | Sacktor et al. |
| 2008/0075722 A1 | 3/2008 | Depinho et al. |
| 2010/0092578 A1 | 4/2010 | Fields et al. |

OTHER PUBLICATIONS

Von Hoff et al, New Eng J Med 361:1164-72, 2009.*
Epstein "Basal cell carcinomas: attack of the hedgehog", Nature Reviews Cancer (2008) 8:743-754.
Erdogan et al. "Aurothiomalate inhibits transformed growth by targeting the PB1 domain of protein kinase Ciota", The Journal of Biological Chemistry (2006) 281(38):28450-9.
Fields et al. "Targeting the oncogenic protein kinase C1 signaling pathway for the treatment of cancer", Biochemical Society Transactions (2007) 35(5):996-1000.
Lauth et al. "Phorbol esters inhibit the Hedgehog signalling pathway downstream of Suppressor of Fused, but upstream of Gli", Oncogene (2007) 26:5163-5168.
Mao et al. "A critical role of Sonic Hedgehog signaling in maintaining the tumorigenicity of neuroblastoma cells", Cancer Sci (2009) 100(10):1848-1855.
Neill et al. "Loss of Protein Kinase Ca Expression May Enhance the Tumorigenic Potential of Gli1 in Basal Cell Carcinoma", Cancer Res. (2003) 63:4692-4697.
Pillai et al. "A novel PKC-1 inhibitor abrogates cell proliferation and induces apoptosis in neuroblastoma", The International Journal of Biochemistry & Cell Biology (2011) 43:784-794.
Yang et al. "Activation of the hedgehog-signaling pathway in human cancer and the clinical implications", Oncogene (2009) 29:469-481.

* cited by examiner

*Primary Examiner* — Lei Yao
(74) *Attorney, Agent, or Firm* — Edward J. Baba; Shweta Chandra; Bozicevic, Field & Francis LLP

(57) ABSTRACT

Methods and compositions are provided for modulating Hedgehog (Hh) pathway signaling in a cell. Aspects of the methods include methods for inhibiting Hh pathway-promoted cancer proliferation and/or metastasis that is promoted by Hh pathway signaling, methods for treating cancers promoted by Hh pathway signaling, and methods for screening candidate agents for the ability to treat a cancer promoted by Hh pathway signaling. In addition, reagents and kits thereof that find use in practicing the subject methods are provided.

12 Claims, 19 Drawing Sheets

SEQUENCE LISTING

<160> NUMBER OF SEQ ID NOS: 52

<210> SEQ ID NO 1
<211> LENGTH: 9
<212> TYPE: DNA
<213> ORGANISM: homo sapiens

<400> SEQUENCE: 1 tgcccccca                                                                9

<210> SEQ ID NO 2
<211> LENGTH: 9
<212> TYPE: DNA
<213> ORGANISM: homo sapiens

<400> SEQUENCE: 2 gaccccaa                                                                 9

<210> SEQ ID NO 3
<211> LENGTH: 9
<212> TYPE: DNA
<213> ORGANISM: homo sapiens

<400> SEQUENCE: 3 taccccaaa                                                                9

<210> SEQ ID NO 4
<211> LENGTH: 14
<212> TYPE: PRT
<213> ORGANISM: Artificial Sequence
<220> FEATURE:
<223> OTHER INFORMATION: synthetic peptide

<400> SEQUENCE: 4

Ser Ile Tyr Arg Arg Gly Ala Arg Arg Trp Arg Lys Leu Tyr
 1               5                  10

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
agcccggacc acccacgaga a                                                 21

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 6
agcccggagg aggcacgaga a                                                 21

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 7
ccgttcacca tgaaatggat a                                                    21

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
ccagacagaa agcaggttgt t                                                    21

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 9
ggaagaacca ctcctaccaa tactca                                               26

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 10
gtgtttaaat taatgtagag gccttctg                                             28

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
acaaaaggaa cggaaagtgt                                                      20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
agcacgttcc tccagtttac                                                      20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ccaggctctc tctaacaagc                                                      20

<210> SEQ ID NO 14
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 14
acaacattat cgctgggaat                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
caaaagctcc attctcacaa                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
aggaaactgg gagaacatca                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ctaccaagcg tgcctaaagt                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
tttatcccag ggagctaaag                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
taaaagggca cacttgaaaa                                              20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
aattgctgca gaccctaaat                                              20
```

<210> SEQ ID NO 21
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 21
agaaggactc ctatgtgggt ga                                        22

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
actgacctgg gtcatctttt c                                         21

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
acaactttgg cattgaggaa                                           20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
gatgcaggga tgatgttctg                                           20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
ttggtcctga gaggctgaag                                           20

<210> SEQ ID NO 26
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 26
gttggacagc gatcattgc                                            19

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 27
ggctgcgaag atggctctcc                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gtaccacttc cttgaattgg                                              20

<210> SEQ ID NO 29
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 29
aaggaacgat tgggttgtca ccct                                         24

<210> SEQ ID NO 30
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 30
aagggtggaa ccacctgctt ttgct                                        25

<210> SEQ ID NO 31
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 31
acatcatcac ggacaaccct gaca                                         24

<210> SEQ ID NO 32
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 32
tgtgaggcct tgacagacag gaaa                                         24

<210> SEQ ID NO 33
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
gcagggcaag aggattatga c                                            21

<210> SEQ ID NO 34
```

```
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 34
tctcaggcac ccactttc                                                      19

<210> SEQ ID NO 35
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 35
tgctgaacag tcaccctgat ccaa                                               24

<210> SEQ ID NO 36
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 36
accacatgac ttgggtcttc acct                                               24

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37
atgacggtat ggttgactgc gaga                                               24

<210> SEQ ID NO 38
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 38
ccggccaact cttgctttct caat                                               24

<210> SEQ ID NO 39
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 39
gtttaaccag cccaactgtg ccat                                               24

<210> SEQ ID NO 40
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 40
```
aggtccgcac agcttgtttc tttg                                              24

<210> SEQ ID NO 41
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 41
tgtgtattta cggcaggagc agga                                              24

<210> SEQ ID NO 42
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 42
aatgtctccg ttcctccact tggt                                              24

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
ctgggcttct acattcgaga                                                   20

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
tgacagtgac gatgaggttg                                                   20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
ccagcgttta accttcaaga                                                   20

<210> SEQ ID NO 46
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
tgaccatacc ctttgaggaa                                                   20

<210> SEQ ID NO 47
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 47
tgccaagcta atctgtaggg                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
gaatgggcga atcctaaaat                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
ggagtgtgag ctgccataga                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
gggaagtcac tagggatgga                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
ctaagcaccg gcaaattaaa                                              20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
ggtggttagt gcccatagtg                                              20
```

INHIBITORS OF ATYPICAL PROTEIN KINASE C AND THEIR USE IN TREATING HEDGEHOG PATHWAY-DEPENDENT CANCERS

CROSS REFERENCE TO RELATED APPLICATIONS

This application is a continuation of U.S. patent application Ser. No. 13/422,936, now issued U.S. Pat. No. 9,073,964, which application pursuant to 35 U.S.C. §119 (e), claims priority to the filing date of the U.S. Provisional Patent Application Ser. No. 61/483,393 filed May 6, 2011; the disclosure of which is herein incorporated by reference.

GOVERNMENT RIGHTS

This invention was made with government support under contract numbers AR046786 and AR052785 awarded by the National Institutes of Health. The Government has certain rights in the invention.

FIELD OF THE INVENTION

This invention pertains to therapeutics to treat Hh pathway-associated cancers and disorders.

BACKGROUND OF THE INVENTION

The Hedgehog (Hh) signaling pathway plays a critical role in development and tumorigenesis across metazoa. Three mammalian Hh genes have been identified: Sonic hedgehog (SHh), Desert hedgehog (DHh), and Indian hedgehog (IHh). These proteins are secreted proteins that act by antagonizing the receptor Patched (Ptch1 or Ptch2 in humans). Ptch acts in part by antagonizing the activity of Smoothened (Smo), a G-protein coupled receptor that activates the transcription factor Gli. When Shh binds to Ptch, Ptch-mediated repression of Smo is relieved, allowing Smo to promote Gli-dependent transcription. During development, Hh induced Smo activity promotes proliferation, migration, and differentiation of progenitor cells to pattern organ development. However, disregulation of Hh pathway signaling, for example by inactivating mutations of Ptch or activating mutations of Smo, has been associated with cancer (Toftgard, R. Hedgehog signalling in cancer. Cell Mol. Life Sci., 57: 1720-1731 (2000)). Induction of Hh target genes is required for tumor growth and maintenance in tumor epithelia, and Hh pathway signaling has been implicated in tumor metastasis of a number of epithelial tumors. For example, basal cell carcinoma (BCC) initiation and expansion requires high levels of Hh pathway signaling. What is needed are novel regulators of the Hedgehog signaling pathway. The present invention addresses these issues.

SUMMARY OF THE INVENTION

Methods and compositions are provided for modulating Hedgehog (Hh) pathway signaling in a cell. Aspects of the methods include methods for inhibiting Hh pathway-promoted cancer proliferation and/or metastasis that is promoted by Hh pathway signaling, methods for treating cancers promoted by Hh pathway signaling, and methods for screening candidate agents for the ability to treat a cancer promoted by Hh pathway signaling. In addition, reagents and kits thereof that find use in practicing the subject methods are provided.

In some aspects of the invention, a method of inhibiting Hedgehog (Hh) pathway-promoted cancer cell proliferation and/or metastasis is provided, the method comprising contacting a cancer cell in which the Hh pathway is activate with an aPKC iota antagonist in an amount effective to inhibit Hh pathway-induced proliferation and/or metastasis of the cell. In some aspects of the invention, a method of treating a Hedgehog (Hh) pathway-promoted cancer is provided, the method comprising administering to an individual with a disorder promoted by Hh pathway signaling an aPKC antagonist in an amount effective to inhibit Hh pathway-induced cellular proliferation and/or metastasis. In some embodiments, the disorder is a cancer, e.g. basal cell carcinoma (BCC), medulloblastoma, rhabdomyosarcoma, small cell lung cancer, pancreatic cancer, prostate cancer, colorectal cancer, or ovarian cancer. In some embodiments, the disorder is Basal Cell Nevus Syndrome The aPKC antagonist may be a peptide, a small molecule, or an siRNA. In some embodiments, the cell comprises a constitutively active Hh pathway. In some embodiments, the cell is resistant to inhibitors that antagonize other members of the Hh pathway, e.g. inhibitors of Smo. In some in vivo embodiments, the aPKC antagonist is coadministered with a cancer therapy. In some in vivo embodiments, the aPKC antagonist is administered topically.

In some aspects of the invention, an isolated pseudosubstrate inhibitor of aPKC iota which specifically suppresses Hh pathway-promoted cancer cell proliferation and metastasis is provided. In some aspects, a pharmaceutical composition is provided that consists essentially of this pseudosubstrate inhibitor of aPKC iota.

In some aspects of the invention, a method of screening a candidate agent for the ability to treat a cancer promoted by Hh pathway signaling is provided, the method comprising measuring the activity of atypical PKC iota in the presence of the candidate agent, and comparing the atypical PKC iota activity to atypical PKC iota activity in the absence of the candidate agent, wherein an inhibition of aPKC iota activity indicates that the candidate agent will treat a cancer promoted by Hh pathway signaling. In some embodiments, the activity of atypical PKC iota is measured in a cell-free system. In other embodiments, the activity of atypical PKC iota is measured in a cell-based system.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
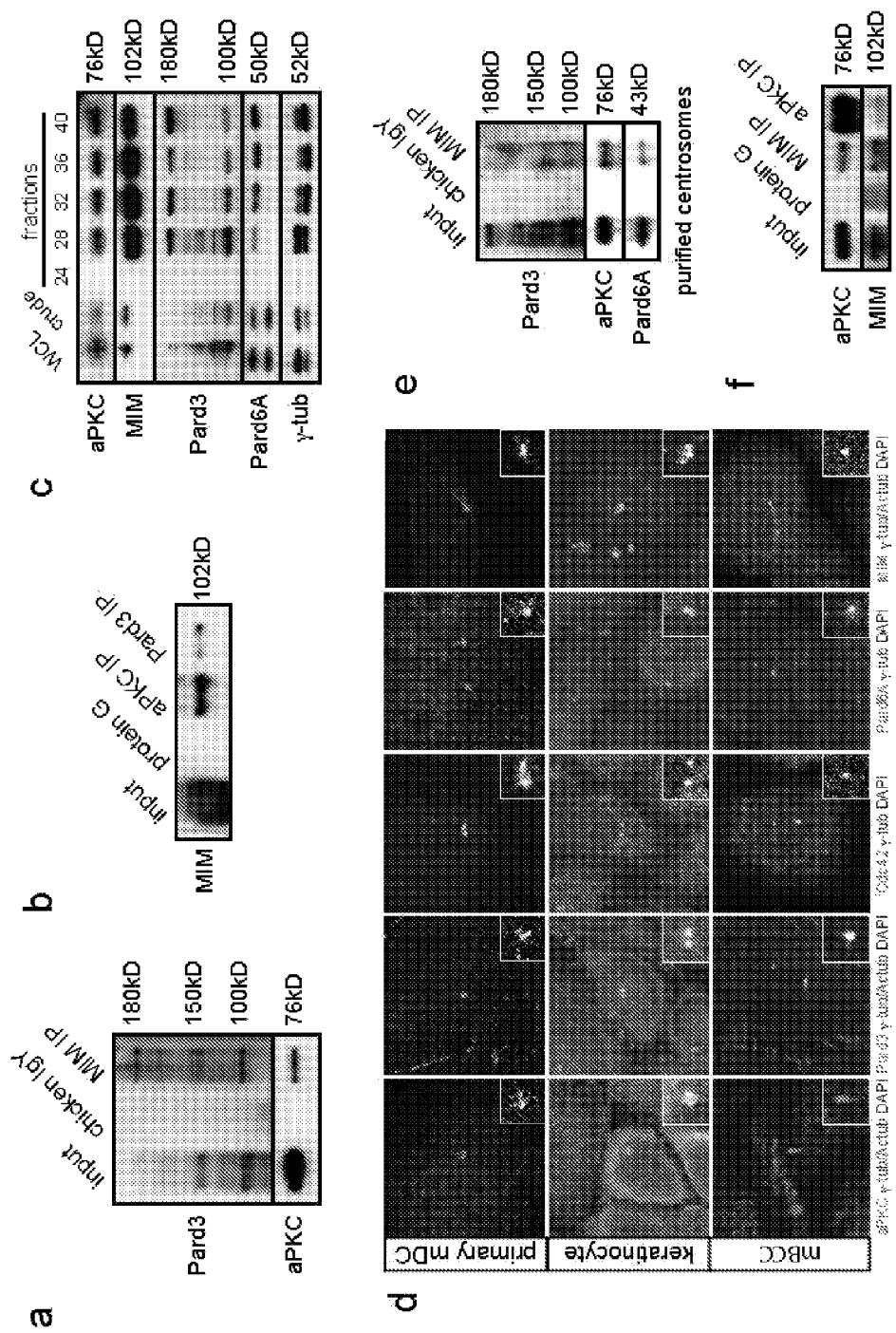
FIG. 1 demonstrates that aPKC is a centrosome-associated protein that regulates Hh signaling. a, b, Reciprocol immunoprecipitation of MIM-aPKC-Pard3 complexes in mouse dermal cell lysate. c, Cofractionation of MIM-aPKC-Pard3-Pard6A in purified centrosome fractions from mouse fibroblasts. WCL, whole cell lysate. d, Immunofluorescence of MIM and aPKC complex members at the centrosome of primary mouse dermal cells (mDC), mouse keratinocytes, and mouse BCC cells. γ-tub, γ-tubulin. Actub, acetylated tubulin. e, f, Immunoprecipitation of MIM-aPKC complexes from (e) purified centrosomes and (f) BCC cells. g, h, j, gli1 mRNA levels or cilia percentage after shRNA knockdown of MIM, aPKC, or inhibition of aPKC (PSI) in BCC cells. i, Cell proliferation levels reduced in BCC cells after incubation with increasing amounts of PSI or cyclopamine. k, aPKC inhibition and shRNA knockdown do not amplify loss of Hh signaling. l, m, Hh signaling and ciliogenesis are separable in nonpolar primary mouse dermal cells after shRNA knockdown of aPKC. Error bars, s.e.m.
Figure 1:
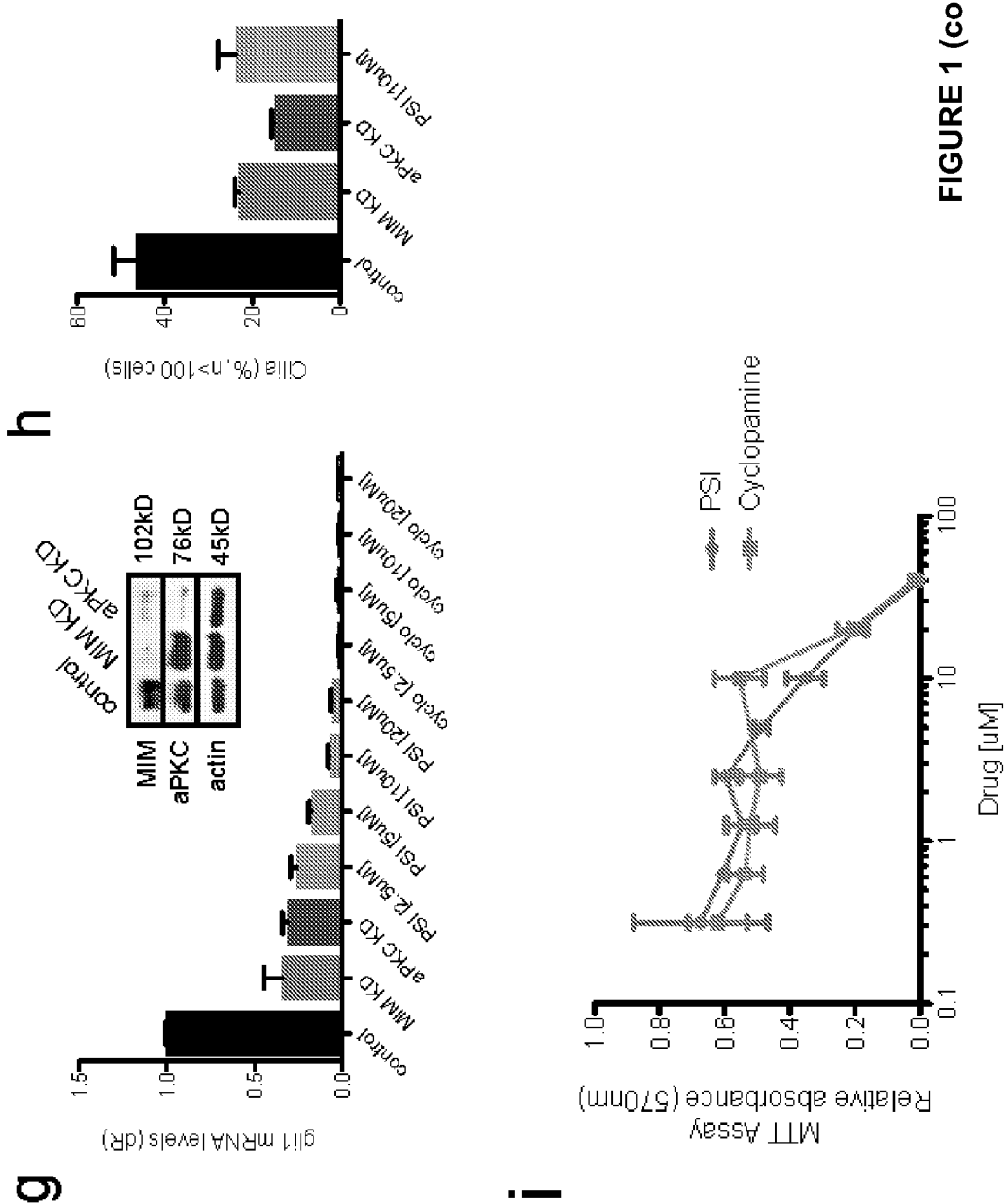
Figure 1:
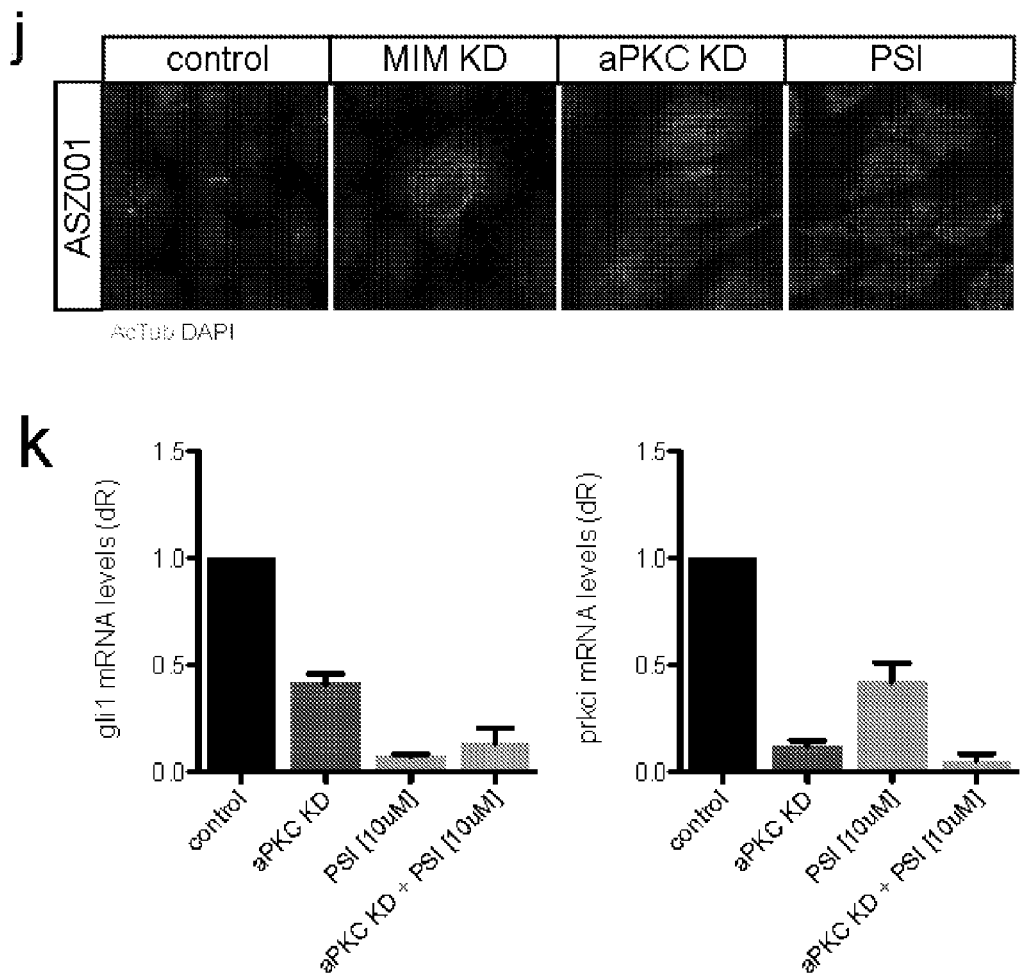
Figure 1:
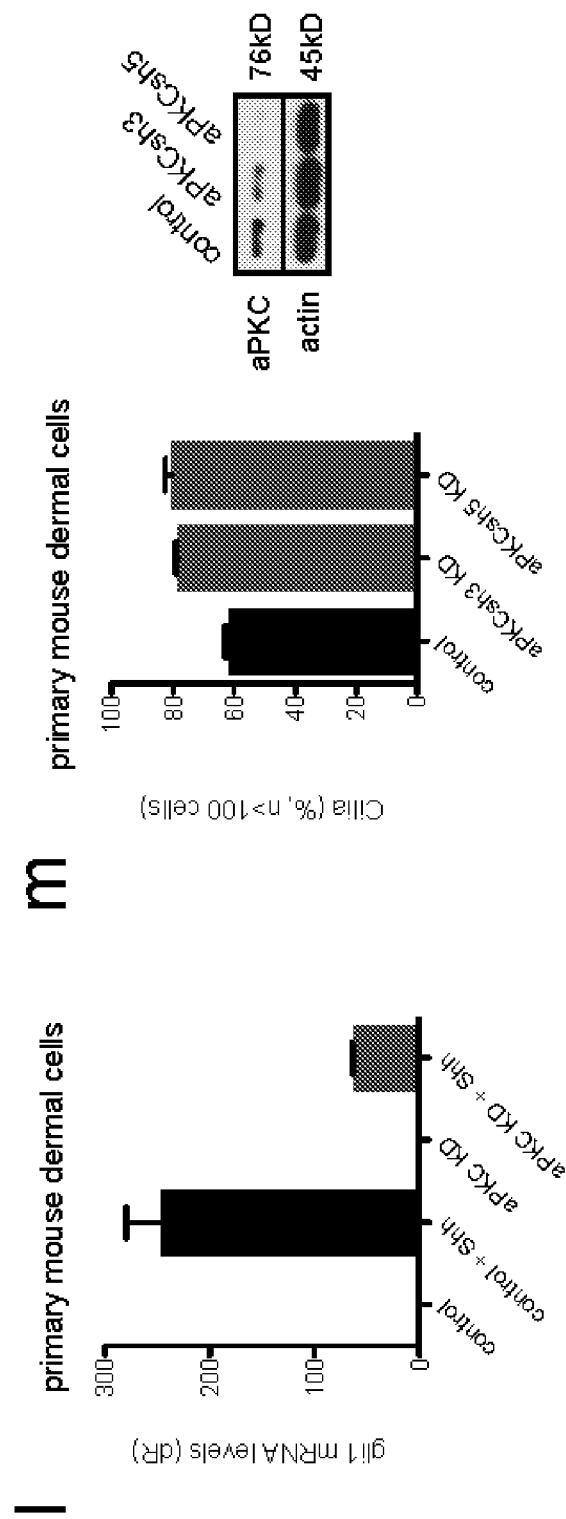

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for modulating Hedgehog (Hh) pathway signaling in a cell. Aspects of the methods include methods for inhibiting Hh pathway-promoted cancer proliferation and/or metastasis that is promoted by Hh pathway signaling, methods for treating cancers promoted by Hh pathway signaling, and methods for screening candidate agents for the ability to treat a cancer promoted by Hh pathway signaling. In addition, reagents and kits thereof that find use in practicing the subject methods are provided. These and other objects, advantages, and features of the invention will become apparent to those persons skilled in the art upon reading the details of the compositions and methods as more fully described below.

In aspects of the invention, methods and compositions are provided for modulating Hedgehog (Hh) pathway signaling in a cell. The Hedgehog (Hh) pathway is a signaling pathway that is activated in healthy cells by Hh ligand. Three Hedgehog ligands have been identified in mammals to date: Sonic hedgehog (SHh), Desert hedgehog (DHh), and Indian hedgehog (IHh). By a Hh signaling pathway, it is meant a signaling pathway that is normally activated by any of these hedgehog ligands or homologs or variants thereof. It has been observed that the activity of this signaling pathway may become disregulated, for example, active in the absence of Hedgehog ligands, or inactive in the presence of Hedgehog ligands. In aspects of the invention, methods and compositions are provided for modulating Hh pathway signaling under normal circumstances as well as under circumstances in which the pathway has become disregulated.

In some methods of the invention, Hh pathway signaling is inhibited. By inhibited, it is meant the activity of the pathway is reduced, suppressed, decreased, attenuated or antagonized. For example, it may be desirous to inhibit Hh pathway signaling in a cell in which the Hh pathway is constitutively active, e.g. in a cell that comprises an activating mutation in a Smo gene or an inactivating mutation in a Ptch gene, e.g. a cancerous cell. Other mutations in the Hh signaling pathway that would promote constitutive activity of the Hh signaling pathway are well known or could be readily determined by the ordinarily skilled artisan.

In other methods of the invention, Hh pathway signaling is promoted. By promoted it is meant the activity of the pathway is activated, increased, or enhanced. For example, it may be desirous to promote Hh pathway signaling in a cell in which the Hh pathway is inactive, e.g. in a cell that comprises an inactivating mutation for Hh, e.g. in a tissue that requires Hh pathway signaling to develop normally.

Compositions that Modulate Hh Pathway Signaling

To modulate Hh pathway signaling in cells, cells are contacted with an aPKC iota modulator. In other words, the cells are contacted with an agent that is a modulator (antagonist or agonist) of aPKC iota activity. aPKC iota, also called PRKCI, PKCI, or protein kinase C iota, is a member of the protein kinase C (PKC) family of serine/threonine protein kinases. The amino acid sequence for human aPKC iota and the nucleic acid sequence that encodes it may be found at GenBank Accession No. NM_002740.5. Agents that modulate aPKC iota activity would include agents that modulate aPKC iota activity directly, i.e. by modulating aPKC iota expression levels or by physically interacting with aPKC protein, as well as agents that modulate aPKC iota activity indirectly, i.e. by modulating the activity of proteins that modulate aPKC iota activity. Examples of such proteins include the intracellular proteins PI3K, PDK1, Src, Bcr-abl and Ras; the cytokines TNF and IL-1; and the growth NGF and EGF. Agents that modulate the activity of any of these proteins would modulate the activity of aPKC, and as such would find use as aPKC modulators in the subject methods.

In embodiments in which it is desirous to inhibit Hh pathway signaling, a cell is contacted with an aPKC iota antagonist. By an aPKC iota antagonist, it is meant an agent that reduces, suppresses or inhibits aPKC iota activity. In other words, an aPKC iota antagonist antagonizes the activating effect of aPKC iota on the Hh signaling pathway. In some embodiments, the aPKC iota antagonist is a polypeptide or peptide. For example, the antagonist may be a peptide that competes with natural substrates for access to the active site of aPKC iota, i.e. a pseudosubstrate inhibitor, or "PSI". In some instance, the PSI is a PSI that is specific for atypical PKCs, i.e. it is specific for aPKC iota and aPKC zeta. In some instances, it is specific for aPKC iota. In some instances, the PSI is a peptide that consists or consists essentially of the sequence SIYRRGARRWRKLY (SEQ ID NO:4), for example a SIYRRGARRWRKLY peptide that has been myristoylated (to make it cell permeable). By "consisting essentially of", it is meant a limitation of the scope of the described composition, method, or kit to the specified materials or steps that do not materially affect the basic and novel characteristic(s) of the subject invention. For example, a peptide "consisting essentially of" a disclosed sequence has the amino acid sequence of the disclosed sequence plus or minus about 5 amino acid residues at the boundaries of the sequence based upon the full length parent substrate sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue. By "consisting of", it is meant the exclusion from the composition, method, or kit of any element, step, or ingredient not specified in the claim. For example, a peptide "consisting of" a disclosed sequence consists only of the disclosed amino acid sequence. As another example, the antagonist may be an endogenous (i.e. naturally occurring) polypeptide inhibitor of aPKC iota, e.g. a native Pard6a polypeptide or active variant or peptide fragment thereof. By "native polypeptide" it is meant a polypeptide found in nature. By "variant" it is meant a mutant of the native polypeptide having less than 100% sequence identity with the native sequence, e.g. 65%, 70%, 75%, or 80% or more identity, such as 85%, 90%, or 95% or more identity, for example, 98% or 99% identity with the full length native polypeptide. As another example, the antagonist may be a polypeptide or peptide inhibitor of an endogenous activator of aPKC iota, e.g. an antagonist of PI3K, PDK1, Src, Bcr-abl, Ras, TNF, IL-1, NGF or EGF. In some embodiments, the antagonist is an aPKC iota-specific antibody, or an antibody that inhibits the activity of an endogenous activator of aPKC iota, e.g. an antibody that is specific for PI3K, PDK1, Src, Bcr-abl, Ras, TNF, IL-1, NGF or EGF. In some embodiments, the aPKC antagonist is a nucleic acid, for example, a nucleic acid that encodes a polypeptide or peptide agonist, or an siRNA that is specific for aPKC iota, e.g. as described in the examples section below. In some embodiments, the aPKC iota antagonist is a small molecule that binds directly to and inhibits aPKC iota activity, e.g. aurothiomalate (ATM), or aurothioglucose (ATG), or that binds directly to and inhibits the activity of an endogenous activator of aPKC iota, e.g. a small molecule inhibitor of PI3K, PDK1, Src, Bcr-abl, Ras, TNF, IL-1, NGF or EGF.

In embodiments in which it is desirous to promote Hh pathway signaling, a cell may be contacted with an aPKC iota agonist. By an aPKC iota agonist it is meant an agent that promotes or enhances the activity of aPKC iota. In other words, an aPKC iota agonist promotes the activating effect of aPKC iota on the Hh signaling pathway. In some embodiments, the aPKC iota agonist is a polypeptide or peptide. For example, the agonist may be a native aPKC iota polypeptide or variant or fragment thereof having kinase activity. As another example, the agonist may be polypeptide or variant or fragment thereof that is a naturally occurring agonist of aPKC iota kinase activity, e.g. a native CDC42 polypeptide or active variant or fragment thereof, a native PI3K polypeptide or active variant or fragment thereof, a native PDK1 polypeptide or active variant or fragment thereof, a native Src polypeptide or active variant or fragment thereof, a native Bcr-abl polypeptide or active variant or fragment thereof, a native Ras polypeptide or active variant or fragment thereof, a native TNF polypeptide or active variant or fragment thereof, a native IL-1 polypeptide or active variant or fragment thereof, a native NGF polypeptide or active variant or fragment thereof or a native EGF polypeptide or active variant or fragment thereof. In some embodiments, the agonist is a nucleic acid, for example a nucleic acid encoding native aPKC iota polypeptide or an active variant or fragment thereof, or a nucleic acid encoding a polypeptide or variant or fragment thereof that is a naturally occurring agonist of aPKC iota kinase activity. Any convenient method may be used to determine if an agent promotes aPKC iota kinase activity. For example, as demonstrated below, the phosphorylation of Gli in the presence of aPKC iota in the absence versus presence of the agent may be assessed.

Methods

In performing the subject methods, the aPKC modulator, i.e. aPKC antagonist or aPKC agonist, is provided to the cells in an effective amount, that is, an amount that is effective to modulate Hh pathway signaling. Biochemically speaking, an effective amount or effective dose of an aPKC modulator is an amount of modulator necessary to alter Hh pathway signaling in a cell by 30% or more, 40% or more, 50% or more, 60% or more, 70% or more, 80% or more, 90% or more, 100% or more, 200% or more, or 500% or more. In other words, the activity of the Hh signaling pathway in a cell contacted with an effective amount or effective dose of a aPKC iota antagonist will be about 70% or less, about 60% or less, about 50% or less, about 40% or less, about 30% or less, about 20% or less, about 10% or less, about 5% or less, or will be about 0%, i.e. negligible, the activity observed in a cell that has not been contacted with an effective amount/dose of a aPKC iota antagonist, while the activity of the Hh signaling pathway in a cell contacted with an effective amount or effective dose of a aPKC iota agonst will be about 30% or more, 40% or more, 50% or more, 60% or more, 70% or more, 80% or more, 90% or more, 100% or more, 200% or more, or 500% or more. Put another way, the Hh pathway signaling will be altered about 0.5-fold or more, 1-fold or more, 2-fold or more, 5-fold or more, 8-fold or more, or 10-fold or more. The amount of modulation of a cell's activity by an aPKC modulator can be determined by a number of ways known to one of ordinary skill in the art of molecular biology. For example, the amount of phosphorylated transcription factor Gli in a cell may be measured by Western blotting; the amount of binding of Gli to DNA target sequence may be measured by electrophoretic mobility assay (EMSA), the amount of expression of transcription factors that are normally activated by Hh signaling, e.g. ptch1, ptch2, hhip1, nhk2, and rab34, may be measured, for example by measuring the RNA or protein levels of genes that are the transcriptional targets of Gli, or by transfecting/infecting the cell with a nucleic acid vector comprising a Gli-responsive promoter operably linked to a reporter protein such as luciferase, EGFP, etc. and qualitatively or quantitatively measuring the amount of reporter protein that is produced. In this way, the modulatory effect of the agent may be confirmed.

In a clinical sense, an effective dose of an aPKC iota modulator is the dose that, when administered for a suitable period of time, usually at least about one week, and maybe about two weeks, or more, up to a period of about 4 weeks, 8 weeks, or longer will evidence an alteration the symptoms associated with undesired activity (or absence thereof) of the Hh signaling pathway. For example, an effective dose of an aPKC iota antagonist is the dose that when administered for a suitable period of time, usually at least about one week, and may be about two weeks, or more, up to a period of about 4 weeks, 8 weeks, or longer will slow, halt or reverse tumor growth and metastasis in a patient suffering from cancer. It will be understood by those of skill in the art that an initial dose may be administered for such periods of time, followed by maintenance doses, which, in some cases, will be at a reduced dosage.

Calculating the effective amount or effective dose of aPKC modulator to be administered is within the skill of one of ordinary skill in the art, and will be routine to those persons skilled in the art. Needless to say, the final amount to be administered will be dependent upon a variety of factors, include the route of administration, the nature of the disorder or condition that is to be treated, and factors that will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally or topically administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The subject methods may be used to modulate Hh pathway signaling—and hence cellular activities associated with Hh pathway signaling—in cells in vitro and in vivo. For example, any cell in which Hh pathway signaling is undesirable, e.g. a cancerous cell in which uncontrolled Hh pathway signaling promotes proliferation or metastasis, or any cell in which Hh pathway signaling is desirable, e.g. a developing cortical neuron that requires Hh pathway signaling to develop, may be contacted with a aPKC iota modulator. Cells may be from any mammalian species, e.g. murine, rodent, canine, feline, equine, bovine, ovine, primate, human, etc.

If the subject methods are performed in vitro, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, may be harvested by apheresis, leukocytapheresis, density gradient separation, etc. As another example, cells, e.g. skin, muscle, bone marrow, spleen, liver, pancreas, lung, intestine, stomach, nervous system tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

As mentioned above, the aPKC iota modulator may be provided to cells as a polypeptide or peptide. Such polypeptides/peptides may optionally be fused to a peptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the aPKC iota modulator polypeptide(s) may be myristoylated or fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

The aPKC iota modulator polypeptide/peptide may be produced by eukaryotic cells or by prokaryotic cells, it may be further processed by unfolding, e.g. heat denaturation, DTT reduction, etc. and may be further refolded, using methods known in the art. Alternatively, a aPKC iota modulator polypeptide/peptide may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are aPKC iota modulator polypeptides/peptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The aPKC iota modulator polypeptide/peptide may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

As mention above, the aPKC iota modulator may be a nucleic acid. mRNA encoding aPKC iota modulators may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) Efficient gene targeting in *Drosophila* by direct embryo injection with zinc-finger nucleases. PNAS 105(50):19821-19826. Alternatively, nucleic acids encoding aPKC iota modulator maybe provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the subject cells. In other words, the cells are contacted with vector comprising the nucleic acid encoding the aPKC iota modulator such that the vector is taken up by the cells. Methods for contacting cells with nucleic acid vectors that are plasmids, such as electroporation, calcium chloride transfection, and lipofection, are well known in the art. For viral vector delivery, the cells are contacted with viral particles comprising the nucleic acid encoding the aPKC iota modulator. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line, the appropriate packaging cell line being selected to ensure that the cells are targeted by the packaged viral particles. Methods of introducing the retroviral vectors comprising the nucleic acid encoding the aPKC iota modulator into packaging cell lines and of collecting the viral particles that are generated by the packaging lines are well known in the art.

Vectors used for providing the nucleic acids encoding a aPKC iota modulator to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing aPKC iota modulator(s) to the subject cells may include nucleic acid sequences that encode for selectable markers in the target cells, so as to identify cells that have taken up the aPKC iota modulator.

As also mentioned above, the aPKC iota modulator may be provided to cells as a small molecule. Small molecule compounds may be dissolved in water or alcohols or solvents such as DMSO or DMF, and diluted into water or an appropriate buffer prior to being provided to cells.

To modulate Hh pathway signaling, the aPKC iota modulator is provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent may be provided to the subject cells one or more times, e.g. one time, twice, three times, or more than three times, and the cells allowed to incubate with the agent for some amount of time following each contacting event e.g. 16-24 hours, after which time the media is replaced with fresh media and the cells are cultured further.

Contacting the cells with the aPKC iota modulator may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of nonhomologous end joining and homologous recombination.

In some applications, the aPKC iota modulator is employed to modulate Hh pathway signaling in vivo, e.g. to inhibit tumor growth or metastasis to treat cancer. In these in vivo embodiments, the aPKC iota modulator is administered directly to the individual. An aPKC iota modulator may be administered by any of a number of well-known methods in the art and described below for the administration of peptides, small molecules and nucleic acids to a subject.

In in vivo methods, an effective amount of an aPKC iota modulator is administered to a subject in need thereof. For example, aPKC iota modulators of specific interest are those that inhibit proliferation and/or metastasis of a cancer in a host when the aPKC iota modulator (in this instance, an aPKC iota antagonist) is administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of the aPKC iota inhibitor composition, the treating clinician's assessment of the medical situation, and other relevant factors. It is expected that the amount will fall in a relatively broad range that can be determined through routine trials. For example, the amount of aPKC iota inhibitor employed to inhibit cancer metastasis is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the aPKC iota inhibitor of its by-products, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of the aPKC iota inhibitor may be topical or via injection, e.g. intravenous, intramuscular, or intratumoral injection or a combination thereof.

The aPKC iota inhibitor may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The aPKC iota inhibitor can also be administered as part of a combination therapy, in which at least one of an immunotherapy, a cancer chemotherapy or a radiation therapy is administered to the subject (as described in greater detail below).

Disposition of the aPKC iota inhibitor and its corresponding biological activity within a subject is typically gauged against the fraction of aPKC iota inhibitor present at a target of interest. For example, a aPKC iota inhibitor once administered can accumulate with a glycoconjugate or other biological target that concentrates the material in cancer cells and cancerous tissue. Thus dosing regimens in which the aPKC iota inhibitor is administered so as to accumulate in a target of interest over time can be part of a strategy to allow for lower individual doses. This can also mean that, for example, the dose of aPKC iota inhibitor that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the $IC_{50}$ of a given aPKC iota inhibitor for inhibiting cell migration. By "$IC_{50}$" is intended the concentration of a drug required for 50% inhibition in vitro. Alternatively, the effective amount can be gauged from the $EC_{50}$ of a given aPKC iota inhibitor concentration. By "$EC_{50}$" is intended the plasma concentration required for obtaining 50% of a maximum effect in vivo. In related embodiments, dosage may also be determined based on $ED_{50}$ (effective dosage). In general, with respect to the aPKC iota inhibitor of the present disclosure, an effective amount is usually not more than 200× the calculated $IC_{50}$. Typically, the amount of an aPKC iota inhibitor that is administered is less than about 200×, less than about 150×, less than about 100× and many embodiments less than about 75×, less than about 60×, 50×, 45×, 40×, 35×, 30×, 25×, 20×, 15×, 10× and even less than about 8× or 2× than the calculated $IC_{50}$. In one embodiment, the effective amount is about 1× to 50× of the calculated $IC_{50}$, and sometimes about 2× to 40×, about 3× to 30× or about 4× to 20× of the calculated $IC_{50}$. In other embodiments, the effective amount is the same as the calculated $IC_{50}$, and in certain embodiments the effective amount is an amount that is more than the calculated $IC_{50}$.

An effect amount may not be more than 100× the calculated $EC_{50}$. For instance, the amount of an aPKC iota inhibitor that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated $EC_{50}$. The effective amount may be about 1× to 30× of the calculated $EC_{50}$, and sometimes about 1× to 20×, or about 1× to 10× of the calculated $EC_{50}$. The effective amount may also be the same as the calculated $EC_{50}$ or more than the calculated $EC_{50}$. The $IC_{50}$ can be calculated by inhibiting cell proliferation and/or cell migration/invasion in vitro. The procedure can be carry out by methods known in the art or as described in the examples below.

Effective amounts of dose and/or dose regimen can readily be determined empirically from assays, from safety and escalation and dose range trials, individual clinician-patient relationships, as well as in vitro and in vivo assays such as those described herein and illustrated in the Experimental section, below. For example, a concentration used for carrying out the subject method in mice ranges from about 1 mg/kg to about 25 mg/kg based on the body weight of the mice. Based on this data, an example of a concentration of the aPKC iota inhibitor that can be employed in human may range about 0.083 mg/kg to about 2.08 mg/kg. Other dosage may be determined from experiments with animal models using methods known in the art (Reagan-Shaw et al. (2007) The FASEB Journal 22:659-661).

Formulations

The aPKC iota modulator can be incorporated into a variety of formulations. More particularly, the aPKC iota modulator may be formulated into pharmaceutical compositions by combination with appropriate pharmaceutically acceptable carriers or diluents.

Pharmaceutical preparations are compositions that include one or more aPKC iota modulator present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the aPKC iota modulator can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

For inclusion in a medicament, the aPKC iota modulator may be obtained from a suitable commercial source. As a general proposition, the total pharmaceutically effective amount of the aPKC iota modulator administered parenterally per dose will be in a range that can be measured by a dose response curve.

aPKC iota modulator-based therapies, i.e. preparations of aPKC iota modulator(s) to be used for therapeutic administration, may be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The aPKC iota modulator-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection. Alternatively, the aPKC iota modulator may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The aPKC iota modulator may be provided in addition to other agents. For example, in methods of treating cancer that is promoted by Hh pathway signaling, an aPKC iota antagonist may be coadministered with other known cancer therapies.

Applications

The subject methods and compositions find many uses. For example, methods for inhibiting Hh pathway signaling by providing an aPKC iota antagonist may be applied to studying cancer cell proliferation and/or cell metastasis in vitro, e.g. for research purposes. The term "cell proliferation" as used herein as it applies to cancerous cells refers to the unregulated division of cells that occurs in neoplasms. The term "metastasis" as used herein refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body. Therefore, the present invention contemplates a method of determining the risk of further growth of one or more cancerous tumors in an organ or body part which is not directly connected to the organ of the original cancerous tumor and/or any steps in a process leading up to that growth. The term "tumor," as used herein, refers to all neoplastic cell growth and proliferation, whether malignant or benign, and all pre-cancerous and cancerous cells and tissues. The terms "cancer," "neoplasm," and "tumor" are used interchangeably herein to refer to cells which exhibit autonomous, unregulated growth, such that they exhibit an aberrant growth phenotype characterized by a significant loss of control over cell proliferation.

As another example, the subject methods may be applied to inhibiting cell proliferation and/or cell metastasis in vivo, e.g. to treat cancers that are promoted by Hh pathway signaling, e.g. cancers associated with disregulation/constitutive activity of the Hh signaling pathway, including variants of such cancers that are resistant to and/or have developed a resistance to Hh antagonists, e.g. Smo antagonists, e.g. cyclopamine or vismodegib. The terms "treatment", "treating" and the like are used herein to generally mean obtaining a desired pharmacologic and/or physiologic effect in an individual. The terms "individual," "subject," "host," and "patient," are used interchangeably herein and refer to any mammalian subject for whom diagnosis, treatment, or therapy is desired, particularly humans. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

In general, cells of interest for study and treatment in the present application include precancerous (e.g., benign), malignant, pre-metastatic, metastatic, and non-metastatic cells, where the cancerous phenotype is promoted by Hh pathway signaling. In other words, Hh pathway signaling (and in many instances, unregulated Hh pathway signaling) predisposes cells in the individual to become cancerous, or induces or enhances the symptoms of cancer in the individual, for example tumor growth and metastasis. In many such instances, Hh pathway signaling is elevated in tumor cells relative to the level of signaling observed in a healthy cell, e.g. 2-fold or more, 3-fold or more, 4-fold or more, 6-fold or more, 8-fold or more, 10-fold or more, 20-fold or more, or 50-fold or more over the amount of Hh pathway signaling in a healthy cell. The level of Hh signaling may be measured by any convenient method, e.g. as known in the art or as described herein.

One example of a cancer that is promoted by disregulated Hh pathway signaling is basal cell carcinoma (BCC). BCC tumors have increased Gli levels, and molecularly targeted drugs against BCC have focused on antagonizing Smo and reducing Gli mRNA. One such example is cyclopamine, a plant alkaloid that inhibits Smo. Model systems (in vitro and in vivo) showed that cyclopamine effectively inhibited BCCs, but clinical applications of cyclopamine showed severe side effects that would preclude its use. Another Smo antagonist that has shown good efficacy in metastatic BCC tumors is vismodegib. Other treatments include surgery, chemotherapy, immunotherapy such as *Euphorbia peplus*, Imiquimod, Aldara, and radiation. In some instances, the BCC is resistant to Smo antagonists, for example, the activating mutation in the Hh pathway is downstream or epistatic to Smo, or the cancer cells have developed a resistance to Smo antagonists. The subject methods may be applied to such cancers. Another example of a disorder that is promoted by disregulated Hh pathway signaling is Basal Cell Nevus Syndrome (BCNS) also known as Gorlin Syndrome, a rare multi-system disease whose hallmark is the development of dozens to hundreds of BCCs. Subjects who have BCNS have inherited one defective copy of PTCH1. BCNS is an orphan disease with a prevalence of 1 case per 56,000-164,000 in the population with no effective and tolerable treatments. Consequently, drugs that treat or prevent BCC tumors are of interest for subjects with BCNS.

The subject methods and compositions find use in treating or preventing BCCs in two clinical populations: i) patients with hereditary BCC tumors, e.g., patients with Basal Cell Nevus Syndrome; and ii) patients in the general population with sporadic BCC tumors. In the United States, BCC is the most common cancer diagnosed with 1 million new cases per year. Though BCCs are rarely fatal, their high incidence and frequent recurrence in affected individuals can cause significant morbidity. Currently, the incidence of skin cancer is increasing yearly and treatment of skin cancer imposes a huge burden on national health services. Currently, there is no effective therapy for BCC prevention as sunscreens have not been shown to reduce BCC development in a randomized controlled trial.

Another example of a cancer that is promoted by disregulated Hh pathway signaling is medulloblastoma. Medulloblastoma is a highly malignant primary brain tumor that originates in the cerebellum or posterior fossa. Medulloblastoma is the most common malignant brain tumor, comprising 14.5% of newly diagnosed cases. Medulloblastomas usually form in the vicinity of the fourth ventricle, between the brainstem and the cerebellum. Known therapies for medulloblastoma include chemotherapy, e.g., one or more of lomustine, cisplatin, carboplatin, vincristine or cyclophosphamide, and vismodegib. The subject methods may be applied to medulloblastomas that are resistant to (or have developed a resistance to) Smo antagonists. Another example of a cancer that is promoted by disregulated Hh pathway signaling is rhabdomyosarcoma. Rhabdomyosarcoma is a sarcoma (cancer of connective tissues) in which the cancer cells are thought to arise from skeletal muscle progenitors. It can be found in any anatomic location. Most occur in areas naturally lacking in skeletal muscle, such as the head, neck, and genitourinary tract. Diagnosis of rhabdomyosarcoma depends on recognition of differentiation toward skeletal muscle cells. The proteins myoD1 and myogenin are transcription factor proteins normally found in developing skeletal muscle cells which disappears after the muscle matures and becomes innervated by a nerve. Thus, myoD1 and myogenin are not usually found in normal skeletal muscle and serve as a useful immunohistochemical marker of rhabdomyosarcoma. Treatment for rhabdomyosarcoma consists of chemotherapy, radiation therapy and sometimes surgery.

Hedgehog pathway-dependent cancers in other tissues, including Hedgehog pathway-dependent cancer variants in other tissues that are resistant to Smo antagonists, may also be treated by the subject methods. These include, for example, subtypes of small cell lung cancer, pancreatic cancer, colorectal cancer, ovarian cancer, and prostate cancer, all of which have been shown to respond to blocking agents of the hedgehog pathway.

Screening Methods.

In some aspects of the invention, methods are provided for screening a candidate agent for the ability to treat a cancer promoted by Hh pathway signaling, e.g. BCC. To that end, it has been shown that aPKC iota modulates Hh pathway signaling, and more particularly, aPKC iota antagonists inhibit Hh pathway signaling. Accordingly, screening for candidate agents that antagonize aPKC iota activity should identify agents that will be useful in inhibiting cancer cell proliferation and/or metastasis induced/enhanced by Hh pathway signaling, which, in turn, will treat cancers promoted by Hh pathway signaling.

For example, in screening assays for biologically active agents, a cell-free, or biochemical, kinase reaction for atypical PKC iota kinase activity may be performed. In such assays, a kinase reaction for aPKC iota activity is performed in the presence of the candidate agent and the kinase activity measured; the measured kinase activity is then compared to the kinase activity in the absence of the candidate agent, where an inhibition of aPKC kinase activity in the presence of the candidate agent indicates that the candidate agent will treat a cancer promoted by Hh pathway signaling. Kinase reactions are well known in the art, and reagents and kits for performing kinase reactions are readily available to the ordinarily skilled artisan. Typically, a kinase substrate is incubated with the kinase of interest in the presence of ATP, and the transfer of phosphate to the substrate is detected by, e.g., radioactive or fluorescent tracer linked to the phosphate, antibody specific for the phosphorylated substrate, etc.

As another example, cell-based assays for candidate agents that inhibit aPKC iota activity may be performed. In one example of a cell-based assay, cells expressing wild-type proteins of the Hh pathway may be contacted with Hh protein and the candidate agent, and the activity of aPKC iota in the presence of candidate agent compared to the activity of aPKC iota in the absence of agent by assessing cellular parameters. As another example of a cell-based assay, cells expressing mutant proteins of the Hh pathway, e.g. Smo comprising activating mutations, or Ptch comprising inactivating mutations, may be contacted with the candidate agent, and the activity of aPKC iota in the presence of candidate agent compared to the activity of aPKC iota in the absence of agent by assessing cellular parameters. Cellular parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. As will be readily apparent to the ordinarily skilled artisan, a number of output cellular parameters may be quantified when screening for agents that modulate the activity of aPKC iota. For example, the phosphorylation of an aPKC iota target sequence, e.g. Gli, may be measured, e.g. by Western blot. As another example, the binding of Gli to chromatin may be measured, e.g. by EMSA. As another example, the expression of Gli target genes may be measured, e.g. by Northern blot, RT-PCR, Western blot, etc. As yet another example, the expression of a reporter downstream of Gli-specific promoter may be measured. Any convenient parameter that reflects the activity of aPKC iota may be measured. In some instances, multiple parameters are measured.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Nucleic acids may be provided as vectors, viruses, or any other convenient method known in the art or described elsewhere herein.

Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

Because the candidate polypeptide agent is being assayed for its ability to inhibit the activity of an intracellular protein, the polypeptide may be myristoylated, or comprise the polypeptide sequences of interest fused to a polypeptide permeant domain.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of biochemical or cell-based reactions, usually in conjunction with biochemical reactions or cells not contacted with the agent. The change in parameters in response to the agent is measured, and the result evaluated by comparison to reference samples, e.g. in the presence and absence of the agent, obtained with other agents, etc.

The agents are conveniently added in solution, or readily soluble form, to the cell-free reaction or medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Reagents and Kits

Also provided are reagents and kits thereof for practicing one or more of the above-described methods. The subject reagents and kits thereof may vary greatly. Reagents and devices of interest include those mentioned above with respect to the methods of modulating Hh pathway signaling, inhibiting cancer cell proliferation and/or metastasis that is promoted by Hh pathway signaling, treating disorders such as cancers that are promoted by Hh pathway signaling, and screening candidate agents for the ability to treat cancer by modulating Hh pathway pathway signaling. Reagents may include one or more of the following: one or more agents that is an agonist or antagonist of aPKC iota; buffer or pharmaceutical excipient into which the agent(s) may be dissolved for contacting cells or administering to an individual; aPKC iota substrates, ATP reagents, and kinase detection reagents for acellular screens for candidate agents for treating Hh pathway dependent cancers; and cells, media, and reagents as discussed above for cell-based screens for candidate agents for treating Hh pathway dependent cancers.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Basal cell carcinoma (BCC) growth requires high levels of Hedgehog (Hh) signaling through the transcription factor Gli1 (Ng, J. M. Y. & Curran, T. The Hedgehog's tale: developing strategies for targeting cancer. Nat Rev Cancer 11, 493-501 (2011)). While inhibitors of the membrane protein Smoothened (Smo) effectively suppress Hh signaling and tumor growth, early tumor resistance illustrates the need for additional downstream targets for therapy (Ng, J. M. Y. & Curran, T. The Hedgehog's tale: developing strategies for targeting cancer. Nat Rev Cancer 11, 493-501 (2011); Yauch, R. L. et al. Smoothened mutation confers resistance to a Hedgehog pathway inhibitor in medulloblastoma. Science 326, 572-574 (2009); Buonamici, S. et al. Interfering with resistance to smoothened antagonists by inhibition of the PI3K pathway in medulloblastoma. Science Translational Medicine 2,51ra70 (2010); Dijkgraaf, G. J. P. et al. Small molecule inhibition of GDC-0449 refractory smoothened mutants and downstream mechanisms of drug resistance. Cancer Research 71, 435-444 (2011)). Here we identify atypical Protein Kinase C iota/lambda (aPKC) as a novel Gli regulator. aPKC and polarity signaling partners Pard3, Pard6a, and Cdc42 (St Johnston, D. & Ahringer, J. Cell polarity in eggs and epithelia: parallels and diversity. Cell 141, 757-774 (2010)) colocalize at the centrosome and form a complex with Missing-in-Metastasis (MIM), a multidomain scaffold protein that potentiates Hh signaling and promotes de novo hair follicle formation (Bershteyn, M., et al. MIM and cortactin antagonism regulates ciliogenesis and hedgehog signaling. Dev. Cell 19, 270-283 (2010); Callahan, C. A. et al. MIM/BEG4, a Sonic hedgehog-responsive gene that potentiates Gli-dependent transcription. Genes & Development 18, 2724-2729 (2004)). Genetic or pharmacological loss of aPKC function blocks Hh signaling and proliferation of BCC cells. aPKC forms a positive feedback loop with Gli, as it is a direct target of Gli1 and exhibits elevated levels in BCCs. Genome-wide transcriptional profiling shows that aPKC and Smo control the expression of similar genes in tumor cells. aPKC functions downstream of Smo to phosphorylate and activate Gli1, resulting in maximal DNA binding and Hh activation. Targeting aPKC demonstrates therapeutic potential as application of a topical aPKC inhibitor suppresses Hh signaling and tumor growth in primary murine BCC tumors and multiple independent Smo-resistant cell lines. These results demonstrate aPKC is critical for Hh-dependent processes and implicates aPKC as a new, tumor selective therapeutic target for the treatment of Hh-dependent cancers Materials and Methods All mouse studies were approved by and conformed to the policies and regulations of the Institutional Animal Care and Use Committees at Stanford University and the Children's Hospital Oakland Research Institute. Ptch1+/−, K14CreER2, p53flox/flox mice were used to develop BCC tumors. Tumors were allografted as previously described (Wang, G. Y. et al. Establishment of Murine Basal Cell Carcinoma Allografts: A Potential Model for Preclinical Drug Testing and for Molecular Analysis. Journal of Investigative Dermatology (2011).doi:10.1038/jid.2011.204). Nine tumors from three mice were treated topically twice daily with 0.8 mg/kg PSI dissolved in DMSO for at least 32 days. Ten tumors from three mice were treated with DMSO twice daily as a control. Mice were euthanized and tumors harvested depending on tumor size that exceeded our animal care guidelines. We measured the change in tumor size with calipers every three to four days. Pairwise comparisons between DMSO and PSI treatment were done using a two-sided unpaired t test with GraphPad Prism software.

Cell Culture.

Primary mouse dermal cells were isolated as previously described (Bershteyn, M., Atwood, S. X., Woo, W.-M., Li, M. & Oro, A. E. MIM and cortactin antagonism regulates ciliogenesis and hedgehog signaling. Dev. Cell 19, 270-283 (2010)). Dermal cells were grown in Amniomax media containing supplement and antibiotics (Invitrogen). ASZ001 cells were grown in 154CF media containing 2% chelated FBS, HKGS supplement, and antibiotics (Invitrogen). Keratinocytes (HPA Culture Collections) were grown in CnT-07 media containing supplement and 0.07 mM CaCl2 (CellNTec). Cells were sterum-starved between 24-48 hrs to induce ciliogenesis. MTT cell proliferation assay was performed using manufacturer's protocol from Invitrogen.

Smo resistant cell lines were generated by treating BCC cells with increasingly higher concentrations of Sant-1 every passage for three weeks. Final resistant cell lines were grown in 60 uM Sant-1. Cyclopamine was used to inhibit Hh signaling to verify Smo resistance.

Antibodies and Immunofluorescence Staining.

Cells were fixed with either 4% paraformaldehyde or 100% methanol for 10 min. 1% normal horse serum and 0.1% Triton X-100 in PBS was used for blocking. Tissues were fixed with 4% paraformaldehyde and embedded in paraffin. 10 um sections were cut and deparaffinized using standard conditions before staining. Tissue sections were blocked using 20% normal horse serum and 0.1% Triton X-100 in PBS. The following antibodies were used: rabbit anti-aPKC (1:500; Santa Cruz Biotechnology), rabbit anti-p-aPKC Thr 410 (1:100; Santa Cruz Biotechnology), rabbit anti-Pard6a (1:100; Santa Cruz Biotechnology), mouse anti-Pard6a (1:100; Santa Cruz Biotechnology), mouse anti-Pard3 (1:500; Millipore), mouse anti-Cdc42 (1:500; Santa Cruz Biotechnology), rabbit anti-MIM (1:1000)1, rabbit anti-g-tubulin (1:500; Sigma), mouse anti-g-tubulin (1:500;

Abcam), mouse anti-acetylated tubulin (1:2000; Sigma), goat anti-Gli2 (1:500; R&D Systems), rat anti-HA (1:1000, Covance), rabbit anti-K167 (1:200; Lab Vision), mouse anti-Gli1 (1:1000; Cell Signaling), and TUNEL stain (Roche). Secondary antibodies were from Invitrogen. Confocal images were acquired on a Leica SP2 AOBS Laser Scanning Microscope with a HCX PL APO 63X oil immersion objective. Images were arranged with ImageJ, Adobe Photoshop, and Adobe Illustrator.

Electrophoretic Mobility Shift Assays.

Electrophoretic mobility shift assay performed by incubation of 50 fmol double-stranded radiolabeled Gli1 oligos (5' AGCCCGGACCACCCACGAGAA 3' (SEQ ID NO: 5)) in binding buffer (25 nM HEPES pH 7.5, 25 mM KCl, 2.5 mM MgCl2, 1 mM DTT, 10% glycerol, 25 nM poly(dI-dC), 5 uM ZnSO4) with IVT Gli1:V5/HIS lysate for 10 min at room temperature. 2 pmol unlabeled Gli1 oligos or Gli1 mutant oligos (5' AGCCCGGAGGAGGCACGAGAA 3' (SEQ ID NO:6)) used as competition. Endogenous aPKC inhibited in reticulocyte lysate with PSI during translation reaction and rescue performed by adding recombinant HIS:aPKC for 15 min before addition of radiolabeled Gli1 oligos. Samples were resolved on 6% acrylamide gel and exposed to a phosphor screen (Molecular Dynamics) and imaged with GE Typhoon 9410.

Protein Purification and Binding Experiments.

All proteins were expressed and purified as previously described (Atwood, S. X., et al. Cdc42 acts downstream of Bazooka to regulate neuroblast polarity through Par-6 aPKC. J. Cell. Sci. 120, 3200-3206 (2007)). In vitro translated proteins were produced using manufacturer's protocol in rabbit reticulocyte lysate from Promega. Endogenous proteins were immunoprecipitated by using 5 ug rabbit antiaPKC, chicken anti-MIM, mouse anti-Pard3, rabbit anti-Pard6a, rat anti-HA, or mouse anti-Flag (Sigma) with protein A/G-conjugated beads according to the manufacturer's protocol (Santa Cruz Biotechnology). Samples were separated by SDS-PAGE and transferred to nitrocellulose, followed by antibody incubations and visualization using chemiluminescent substrate (ThermoScientific). Additional antibodies used for western: mouse anti-actin (1:5000; Sigma), rabbit anti-HSP90 (1:200; Santa Cruz Biotechnology), and mouse anti-p63 (1:200; Santa Cruz Biotechnology). Centrosomes were purified from mouse C3H 10T1/2 cells as previously described (Meigs, T. E. & Kaplan, D. D. Isolation of centrosomes from cultured Mammalian cells. CSH Protoc 2008, pdb.prot5039 (2008). Supernatant fractions isolated by incubation of mouse BCC cells with lysis buffer (10 mM HEPES pH 7.5, 1.5 mM MgCl2, 10 mM KCl, 0.4% NP-40) for 2 min on ice. Nuclei were spun down and washed twice with lysis buffer before equal volume resuspension in PBS and addition of SDS loading buffer.

Kinase Assays.

HIS:aPKC (Abcam) was incubated with GST, GST:Gli1, or GST:Gli1 fragments at 30° C. for 15 min in kinase reaction buffer (20 mM Tris-HCl pH 7.5, 10 mM MgCl2, 1 mM DTT, 10 mM ATP) with 20 nM [g-32P]ATP. The reaction was quenched by addition of SDS loading buffer and heated at 95° C. for 10 min. The protein was resolved by SDS-PAGE and exposed to a phosphor screen (Molecular Dynamics) and imaged with GE Typhoon 9410.

Lentiviral Knockdown and Drug Treatments.

Lentiviral pLKO.1 vector containing short hairpin RNAs (Open Biosystems) to prkci (sh3:CCGTTCACCAT-GAAATGGATA (SEQ ID NO:7), sh5:CCAGACA-GAAAGCAGGTTGTT (SEQ ID NO:8)), or pSicoR-puro vector containing shRNA to MIM1 were used. Lentiviral infection was performed and cells assayed after three days for prkci shRNA and four days for MIM shRNA. Protein knockdown was confirmed by western blot or qRTPCR.

Drug treatments for cells were performed with myristoylated PSI (myr-SIYRRGARRWRKLY (SEQ ID NO:4)), Sant-1 (Tocris Bioscience), cyclopamine (Tocris Bioscience), SAG (EMD), and cyclohexamide (Sigma). Subconfluent ASZ001 cells were serum-starved and inhibitors added for 48 hrs prior to MTT assay and 24 hrs prior to visualize cilia and assay Gli target gene induction. Stability assays performed with ASZ001 preincubated with PSI for one hour before 20 ug/ml cyclohexamide addition at various time points.

Chromatin Immunoprecipitation.

Protein-DNA complexes were captured by fixing ASZ001 cells expressing Flag:Gli1 and preincubated 24 hrs with inhibitors for 10 min with 1% formaldehyde and quenched with 0.125M glycine for 5 min. ChIP was performed using manufacturer's protocol adapted from Upstate. Briefly, cells were lysed for 10 min at 4° C. in lysis buffer (50 mM Hepes pH7.5, 140 mM NaCl, 1 mM EDTA, 10% glycerol, 0.1% NP-40, 0.2% Triton-X100, protease inhibitors [Roche]) and nuclei were pelleted and lysed for 10 min at 4° C. in nuclei lysis buffer (10 mM Tris-HCl pH 8, 100 mM NaCl, 1 mM EDTA, 0.5 mM EGTA, 0.5% N-lauroylsarcosine, protease inhibitors) to obtain DNA. DNA was sheared to a range of 100-600 bp in size by sonicating for 25 min. ChIP-grade Flag antibody-conjugated magnetic beads (Sigma) was incubated with nuclei lysate overnight at 4° C. Beads were washed in RIPA buffer and DNA was reverse crosslinked by incubation at 65° C. overnight in elution buffer (50 mM Tris-HCl pH8, 10 mM EDTA, 1% SDS). RNA and protein was digested with RNase A (0.2 ug/ml; 37° C. for 2 hrs) and proteinase K (0.2 ug/ml; 55° C. for 2 hrs), respectively, and DNA purified by phenol chloroform extraction using standard protocols. Relative fold enrichment was determined by adding DNA to Brilliant II SYBR Green qPCR Master Mix Kit (Agilent Technologies) containing primers to known Gli target sites listed in Table 1. ASZ001 without Flag:Gli1 used as a negative control.

3' End RNA Sequencing.

Library was generated from ASZ001 cells incubated with or without inhibitors for 24 hrs. RNA purified using TRIzol (Invitrogen) and poly A-RNA selected using the micropoly (A)purist kit (Ambion). Heat-sheared 200 ng mRNA for 12 min at 85° C. and performed first-strand cDNA synthesis using Superscript III (Invitrogen) for 1 hr at 50° C. Second-strand synthesis was performed using E. coli DNA Ligase (Invitrogen), E. coli DNA Polymerase I (NEB), and E. coli RNAse H (Epicentre) for 2 hr at 16° C. Added T4 DNA Polymerase (NEB) for an additional 15 min before quenching with EDTA. Purified double-stranded cDNA with Min-Elute Reaction Cleanup Kit (Qiagen). 3' A-tailed using Klenow Fragment 3' to 5' exonuclease (NEB) for 30 min at 37° C. Ligated Illumina linker using T4 DNA Ligase (Enzymatics) overnight at room temperature. Purified 220-300 bp bands using 3% NuSieve GTG agarose (Lonza) and Min-Elute Gel Extraction Kit (Qiagen). Amplified the DNA using Phusion PCR Master Mix (NEB) and 15 cycle PCR program. Purified 220-300 bp bands using 3% NuSieve GTG agarose (Lonza) and MinElute Gel Extraction Kit. Sequenced DNA using Illumina Genome Analyzer IIx.

Aligned 36 bp raw reads with Bowtie using the NCBI37/mm9 reference genome. Differential expression analysis was performed on the 3' exon with the Cufflinks suite using mouse RefSeq gene predictions as a reference transcriptome. Annotated coding transcripts were filtered for significant expression by a RPKM of 25 in at least one sample set. Transcripts that were two-fold or greater changed in drug-treated samples were hierarchically clustered using the Cluster program and visualized in Java Treeview. Transcripts were validated using Brilliant II SYBR Green qRT-PCR Master Mix Kit (Agilent Technologies) with primers listed in the following table. Two-tail p-value between our gene sets and other gene sets calculated using Fisher's Exact Test.

specific interaction (FIG. 1b). As MIM is a centrosome-associated protein that promotes ciliogenesis (Bershteyn, M., Atwood, S. X., Woo, W.-M., Li, M. & Oro, A. E. MIM and cortactin antagonism regulates ciliogenesis and hedgehog signaling. Dev. Cell 19, 270-283 (2010)), we fractionated centrosomes and probed for aPKC complex proteins. aPKC, along with Pard3 and Pard6A, cofractionated with MIM in gamma-tubulin positive fractions that mark cen-

TABLE 1

|  | forward oligo | SEQ ID NO | reverse oligo | SEQ ID NO | source |
|---|---|---|---|---|---|
| ChIP oligos | | | | | |
| nanog | GGAAGAACCACTCCTACCAATACTCA | 9 | GTGTTTAAATTAATGTAGAGGCCTTCTG | 10 | Po et al, 2010 |
| ptch1-1 | ACAAAAGGAACGGAAAGTGT | 11 | AGCACGTTCCTCCAGTTTAC | 12 | Vokes et al, 2007 |
| ptch1-2 | CCAGGCTCTCTCTAACAAGC | 13 | ACAACATTATCGCTGGGAAT | 14 | Vokes et al, 2007 |
| rab34 | CAAAAGCTCCATTCTCACAA | 15 | AGGAAACTGGGAGAACATCA | 16 | Vokes et al, 2007 |
| nkx2-9 | CTACCAAGCGTGCCTAAAGT | 17 | TTTATCCCAGGGAGCTAAAG | 18 | Vokes et al, 2007 |
| hhip1 | TAAAAGGGCACACTTGAAAA | 19 | AATTGCTGCAGACCCTAAAT | 20 | Vokes et al, 2007 |
| actin | AGAAGGACTCCTATGTGGGTGA | 21 | ACTGACCTGGGTCATCTTTTC | 22 | Vokes et al, 2007 |
| gapdh | ACAACTTTGGCATTGAGGAA | 23 | GATGCAGGGATGATGTTCTG | 24 | IDT oligos |
| prkci-p1 | TTGGTCCTGAGAGGCTGAAG | 25 | GTTGGACAGCGATCATTGC | 26 |  |
| prkci-p2 | GGCTGCGAAGATGGCTCTCC | 27 | GTACCACTTCCTTGAATTGG | 28 |  |
| qRTPCR oligos | | | | | |
| prkci | AAGGAACGATTGGGTTGTCACCCT | 29 | AAGGGTGGAACCACCTGCTTTTGCT | 30 | IDT oligos |
| prkcz | ACATCATCACGGACAACCCTGACA | 31 | TGTGAGGCCTTGACAGACAGGAAA | 32 | IDT oligos |
| cdc42 | GCAGGGCAAGAGGATTATGAC | 33 | TCTCAGGCACCCACTTTTC | 34 | IDT oligos |
| sulf1 | TGCTGAACAGTCACCCTGATCCAA | 35 | ACCACATGACTTGGGTCTTCACCT | 36 | IDT oligos |
| mnd1 | ATGACGGTATGGTTGACTGCGAGA | 37 | CCGGCCAACTCTTGCTTTCTCAAT | 38 | IDT oligos |
| efna1 | GTTTAACCAGCCCAACTGTGCCAT | 39 | AGGTCCGCACAGCTTGTTTCTTTG | 40 | IDT oligos |
| acot7 | TGTGTATTTACGGCAGGAGCAGGA | 41 | AATGTCTCCGTTCCTCCACTTGGT | 42 | IDT oligos |
| pard6a | CTGGGCTTCTACATTCGAGA | 43 | TGACAGTGACGATGAGGTTG | 44 | Realtime-primers |
| sox9 | CCAGCGTTTAACCTTCAAGA | 45 | TGACCATACCCTTTGAGGAA | 46 | Realtime-primers |
| slc2a1 | TGCCAAGCTAATCTGTAGGG | 47 | GAATGGGCGAATCCTAAAAT | 48 | Realtime-primers |
| ak1 | GGAGTGTGAGCTGCCATAGA | 49 | GGGAAGTCACTAGGGATGGA | 50 | Realtime-primers |
| gng12 | CTAAGCACCGGCAAATTAAA | 51 | GGTGGTTAGTGCCCATAGTG | 52 | Realtime-primers |

Results

In order to identify new druggable targets in the Hh pathway, we used the scaffold protein MIM, which potentiates Gli-dependent activation downstream of Smo (Callahan, C. A. et al. MIM/BEG4, a Sonic hedgehog-responsive gene that potentiates Gli-dependent transcription. Genes & Development 18, 2724-2729 (2004))o7, as bait in a biased proteomics screen of factors involved in Hh signaling and ciliogenesis. Two of the hits were polarity proteins not previously linked to the Hh pathway, aPKC, a serine-threonine kinase, and Pard3, a scaffold protein and aPKC substrate (FIG. 1a). Reciprocaol immunoprecipitation of aPKC and Pard3 also pulled down MIM suggesting a trosomes (FIG. 1c). MIM forms a complex with aPKC and its partners at the centrosome as MIM immunoprecipitates aPKC, Pard3, and Pard6A from purified centrosome fractions (FIG. 1e) suggesting that aPKC may function with MIM at the basal body. We confirmed the association by demonstrating colocalization of aPKC, Pard3, Pard6A, Cdc42, and MIM at the basal body in dermal fibroblasts and keratinocytes (FIG. 1d). We determined aPKC function in BCCs using the well-characterized cell line derived from mouse BCCs, ASZ001 (Aszterbaum, M. et al. Ultraviolet and ionizing radiation enhance the growth of BCCs and trichoblastomas in patched heterozygous knockout mice. Nat Med 5, 1285-1291 (1999)). aPKC and MIM localize to the centrosome of BCC cells and continue to interact as they coimmunoprecipitate each other (FIG. 1d,f). Loss of MIM or aPKC protein suppressed Hh signaling as mRNA levels of Hh target gene gli1 was reduced and ciliogenesis was inhibited by approximately 50% (FIG. 1g,h,j).

Figure 7:
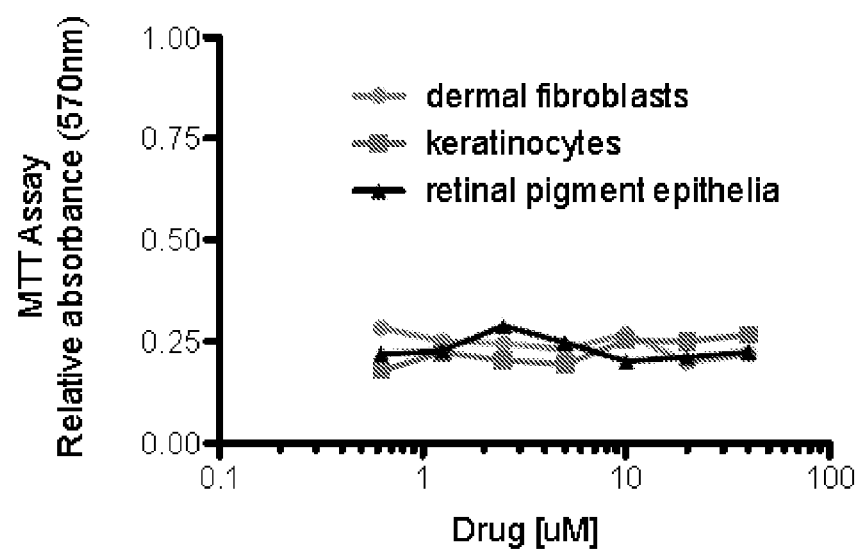
FIG. 7 demonstrates that aPKC inhibition does not affect proliferation of nontumorigenic cells. Cell proliferation levels unchanged in mouse dermal fibroblasts, mouse keratinocytes, and human retinal pigment epithelial cells after incubation with increasing amounts of PSI.

As aPKC kinase activity is necessary for many of its cellular functions (St Johnston, D. & Ahringer, J. Cell polarity in eggs and epithelia: parallels and diversity. Cell 141, 757-774 (2010); Fan, S. et al. Polarity proteins control ciliogenesis via kinesin motor interactions. Curr. Biol. 14, 1451-1461 (2004); Pruliére, G., Cosson, J., Chevalier, S., Sardet, C. & Chenevert, J. Atypical protein kinase C controls sea urchin ciliogenesis. Mol. Biol. Cell 22, 2042-2053 (2011); Ossipova, O. et al. PAR1 specifies ciliated cells in vertebrate ectoderm downstream of aPKC. Development 134, 4297-4306 (2007); Atwood, S. X. & Prehoda, K. E. aPKC phosphorylates Miranda to polarize fate determinants during neuroblast asymmetric cell division. Curr. Biol. 19, 723-729 (2009)), we used a myristoylated aPKC peptide inhibitor (PSI) that competes with substrates for access to the active site to suppress kinase activity. PSI inhibited Hh signaling in BCC cells in a dose-dependent manner similar to the Smo antagonist cyclopamine (FIG. 1g). PSI also resulted in a dose-dependent inhibition of cell growth in BCC cells, leading to cell death as assayed by the MTT assay (FIG. 1i). PSI inhibited cell growth at a concentration similar to that of cyclopamine, with an IC50 of 5 uM. Primary cilia were reduced by 50% in PSI-treated BCC cells (FIG. 1h,j) indicating aPKC activity is critical to both Hh signaling and ciliogenesis in BCC cells. We addressed PSI effects on normal cells and found that proliferation in several non-tumorigenic cells was unaffected (FIG. 7). To verify the specificity of PSI, we knocked down aPKC in BCC cells in combination with PSI treatment and found in this setting that PSI possesses no additional activity to reduce levels of gli1 or apkc mRNA (FIG. 1k), indicating PSI possesses selective aPKC inhibition in BCCs.

To address whether aPKC's effects on the Hh pathway is direct and not dependent on polarity, we assayed aPKC function in several nonpolar cell lines including primary mouse dermal fibroblasts (FIG. 1l,m) and immortalized fibroblast lines (not shown). aPKC knockdown in these cells maintain their primary cilia and in many cases demonstrate increased ciliary length. However, aPKC removal still blocks Hh activation, dramatically reducing target gene induction (FIG. 1l). We conclude that aPKC's effects on Hh signaling are cilia-independent and required for maximal sustained signaling.

Figure 2:
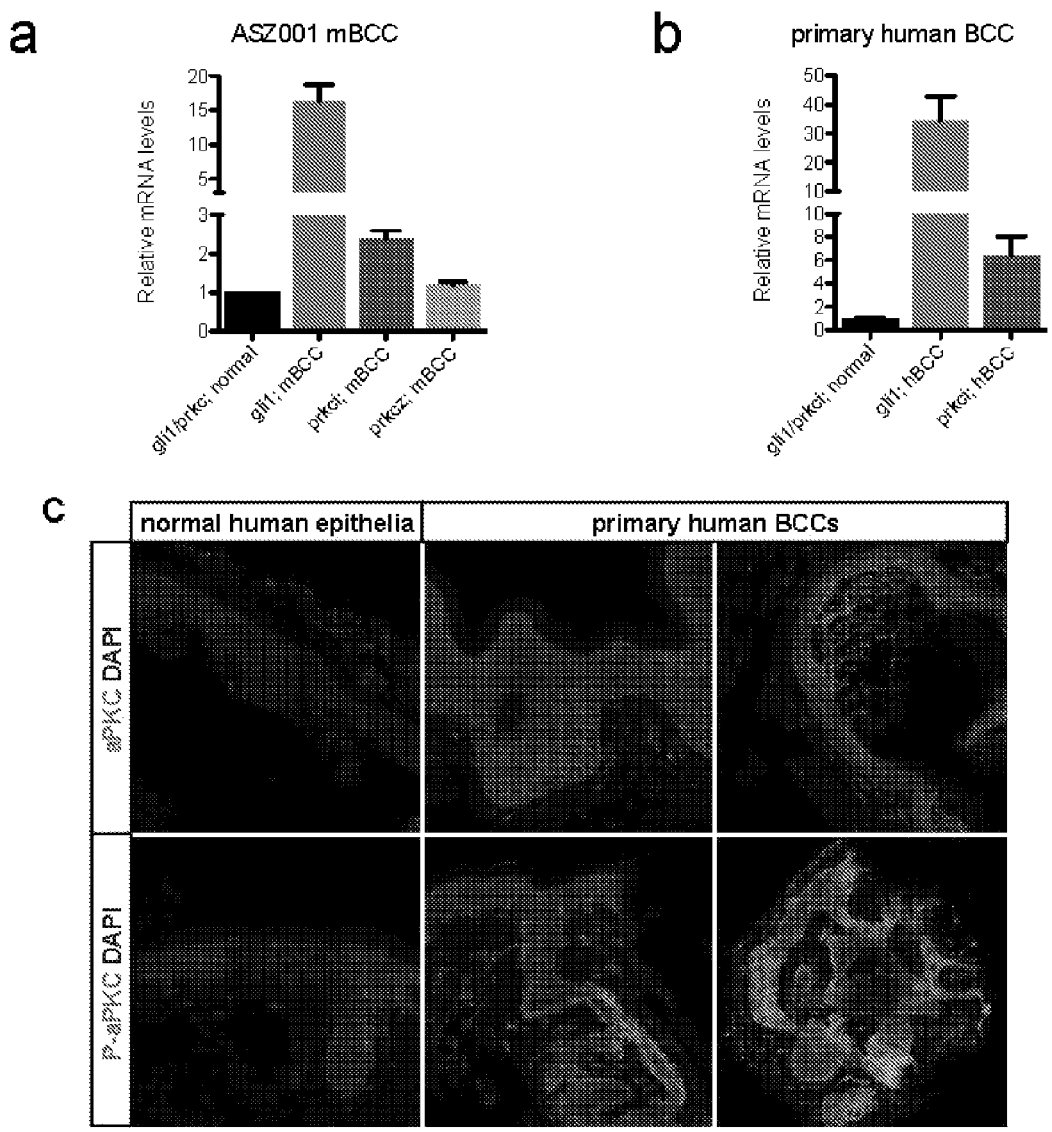
FIG. 2 demonstrates that aPKC and Hh form a positive feedback loop in BCCs. a, b, Relative mRNA levels of gli1, aokciota, or apkczeta in (a) mouse BCC cells and (b) seven independent primary human BCC tumor samples. c, Upregulated protein expression of total and activated aPKC (P-aPKC) in primary human BCC tumor samples. d, apkciota is specifically upregulated in Shh-N-treated primary mouse dermal cells. e, Diagram of putative Gli1 binding sites within the promoter region of aPKC. p1, contains Gli1 binding sites TGCCCCCCA (reverse complement) (SEQ ID NO:1) and GACCCCCAA (SEQ ID NO:2). p2, contains Gli1 binding site TACCCCAAA (reverse complement) (SEQ ID NO:3). TSS, transcriptional start site. f, Flag:Gli1 ChIP of aPKC promoter regions containing Gli1 binding sites. g, apkciota is specifically repressed upon cyclopamine treatment of BCC cells. h, Expression of endogenous aPKC-specific inhibitor (pard6a) is reduced and activator (cdc42) is upregulated in mouse BCC tumors. i, Sant-1-treated mouse BCC cells leads to increased pard6a and decreased cdc42 mRNA expression. Error bars, s.e.m.
Figure 2:
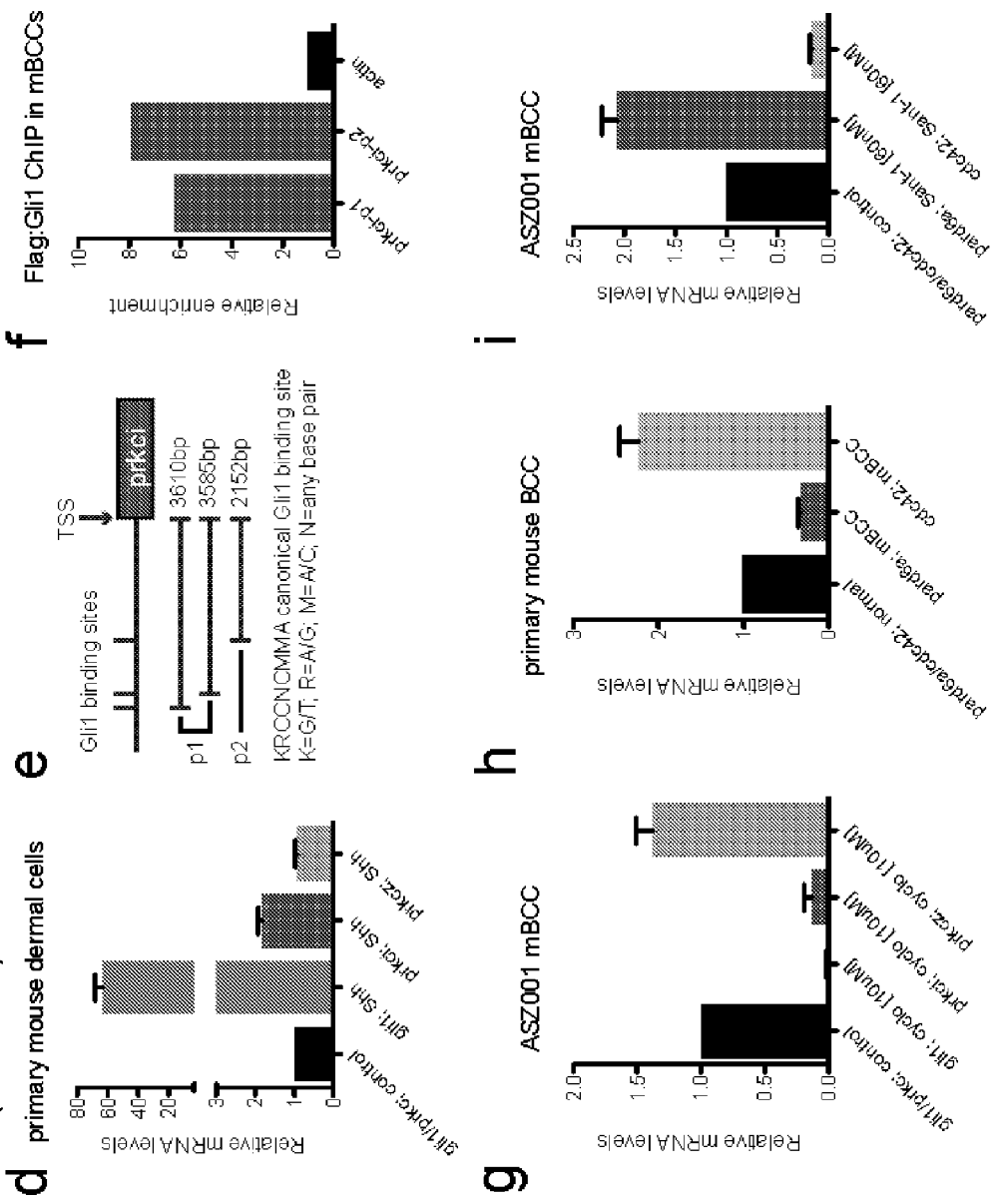

A feature of many morphogen signaling pathways is the presence of positive feedback loops that elevate regulatory proteins (Balaskas, N. et al. Gene regulatory logic for reading the sonic hedgehog signaling gradient in the vertebrate neural tube. Cell 148, 273-284 (2012)). As aPKC is necessary for maximal Hh signaling, we next asked if aPKC is overexpressed in BCCs providing a constant positive signal. Indeed, apkciota expression is specifically upregulated with Hh target gene gli1 in BCC cells (FIG. 2a). By contrast, the zeta isoform is not. Similar results are found using freshly isolated human BCCs compared to primary human keratinocytes (FIG. 2b). Immunohistochemical staining of human BCCs and normal skin with antibodies recognizing both total and activated aPKC (P-aPKC) show markedly higher levels in invasive and nodular tumors, with P-aPKC showing greater overexpression (FIG. 2c).

As aPKC and Hh signaling are required for BCC cell growth, we next asked whether aPKC is a Hh target gene. Activation of Hh signaling in both polarized and non-polarized primary and immortalized cells using Shh-N ligand induces both gli1 and apkciota transcript (FIG. 2d). Additionally, when we block Hh signaling by treating BCC cells with cyclopamine, gli1 and apkciota transcript, and not apkczeta, are specifically suppressed (FIG. 2g). Three putative Gli1 binding sites are present in the promoter region of apkciota (FIG. 2e) (Winklmayr, M. et al. Non-consensus GLI binding sites in Hedgehog target gene regulation. BMC Mol. Biol. 11, 2 (2010)).14 Chromatin immunoprecipitation (ChIP) with BCC cells overexpressing Flag:Gli1 enrich in regions containing the three Gli1 binding sites over negative control (FIG. 2f) indicating that aPKC is a direct target of Gli1. In fact, expression of an endogenous inhibitor of aPKC (Pard6A) is reduced whereas an activator (Cdc42) is overexpressed in primary mouse BCC tumors originating from Ptch1+/−, K14CreER2, p53flox/flox mice (Wang, G. Y. et al. Establishment of Murine Basal Cell Carcinoma Allografts: A Potential Model for Preclinical Drug Testing and for Molecular Analysis. Journal of Investigative Dermatology (2011)) (FIG. 2h). Interestingly, when Hh signaling is inhibited with the Smo antagonist Sant-1, pard6a transcript is elevated and cdc42 is repressed (FIG. 2i) further supporting the idea that the Hh pathway promotes aPKC activation. We conclude that aPKC is part of a Hh-mediated positive feedback loop that is overexpressed in human and mouse BCCs.

Figure 3:
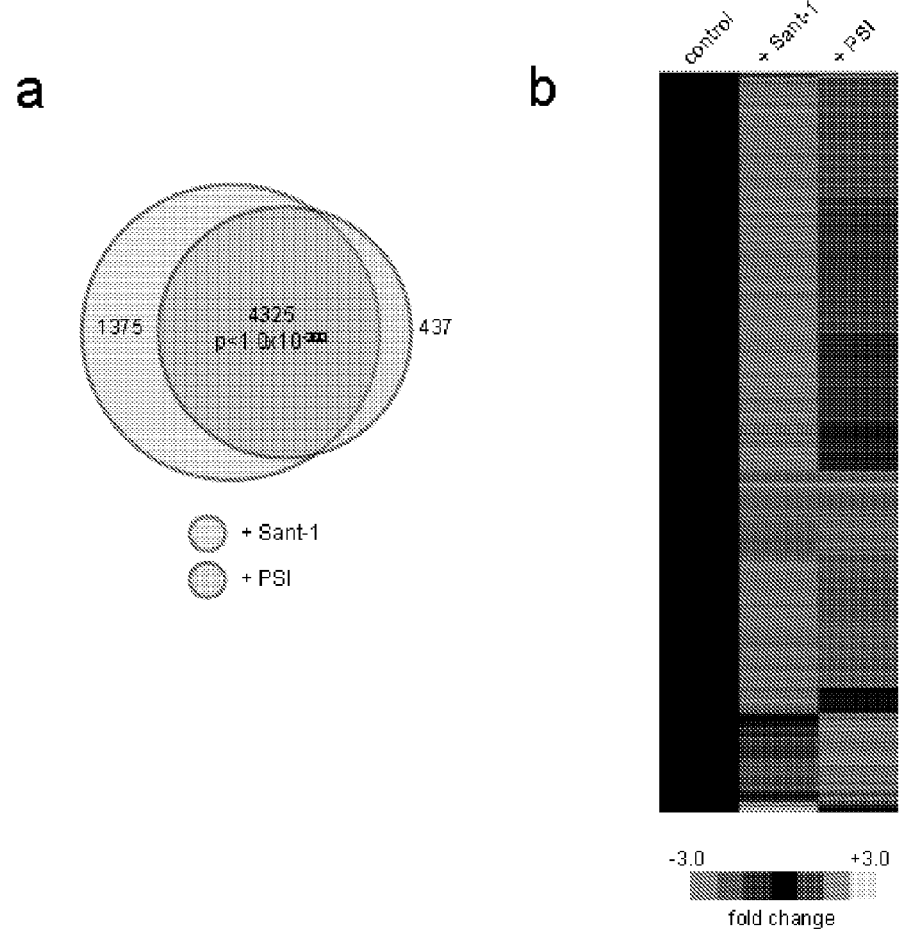
FIG. 3 demonstrates that aPKC phosphorylates and activates Gli1. a, Venn diagram and (b) heatmap of significantly changed transcripts upon treatment with Sant-1 and PSI in mouse BCC cells. Note striking overlap of affected genes. c, Gene ontology terms of commonly altered transcripts. d, SAG does not rescue reduced Hh signaling from PSI-treated BCC cells. Error bars, s.e.m. e, PSI affects activity, but not nuclear Gli protein localization in BCC cells. f, Reciprocal immunoprecipitation of in vitro translated (IVT) human Gli1 or Gli1 DNA-binding domain with aPKC. g, aPKC phosphorylates recombinantly expressed human Gli1 DNA-binding domain. h, Electrophoretic mobility shift assay (EMSA) showing aPKC promotes DNA binding of IVT human Gli1. NS, non-specific binding. i, Densitometry of aPKC rescue in three independent EMSA experiments. j,Flag:Gli1 ChIP showing PSI and Sant-1 inhibit Gli1 binding to target sites in mouse BCC cells.
Figure 3:
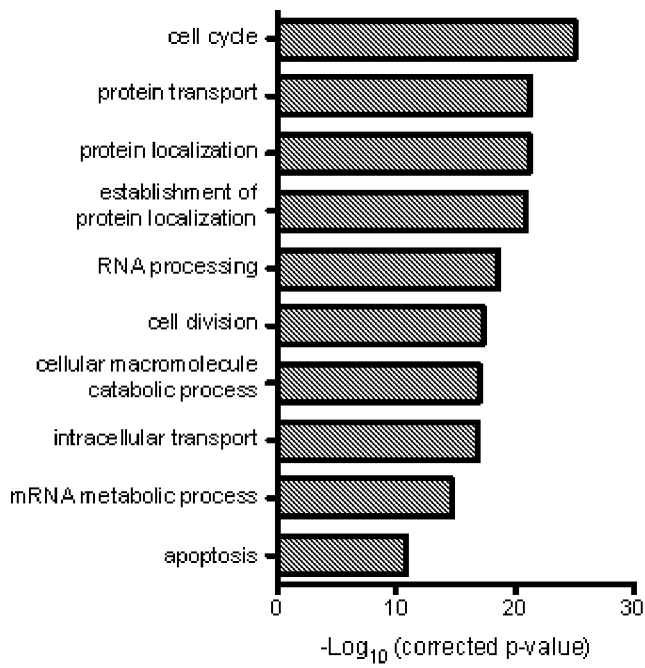
Figure 3:
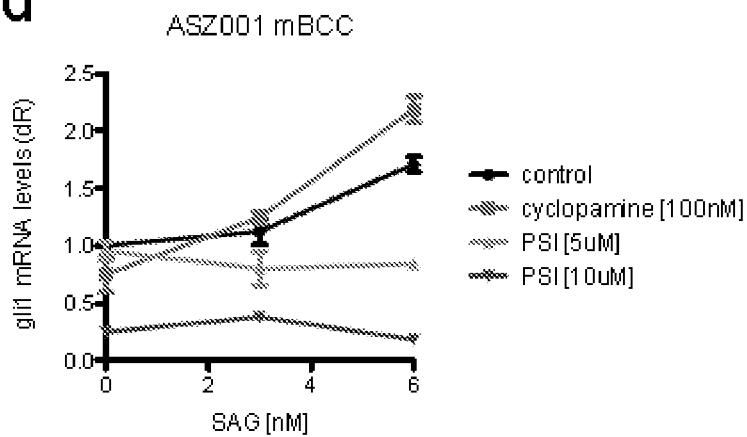
Figure 3:
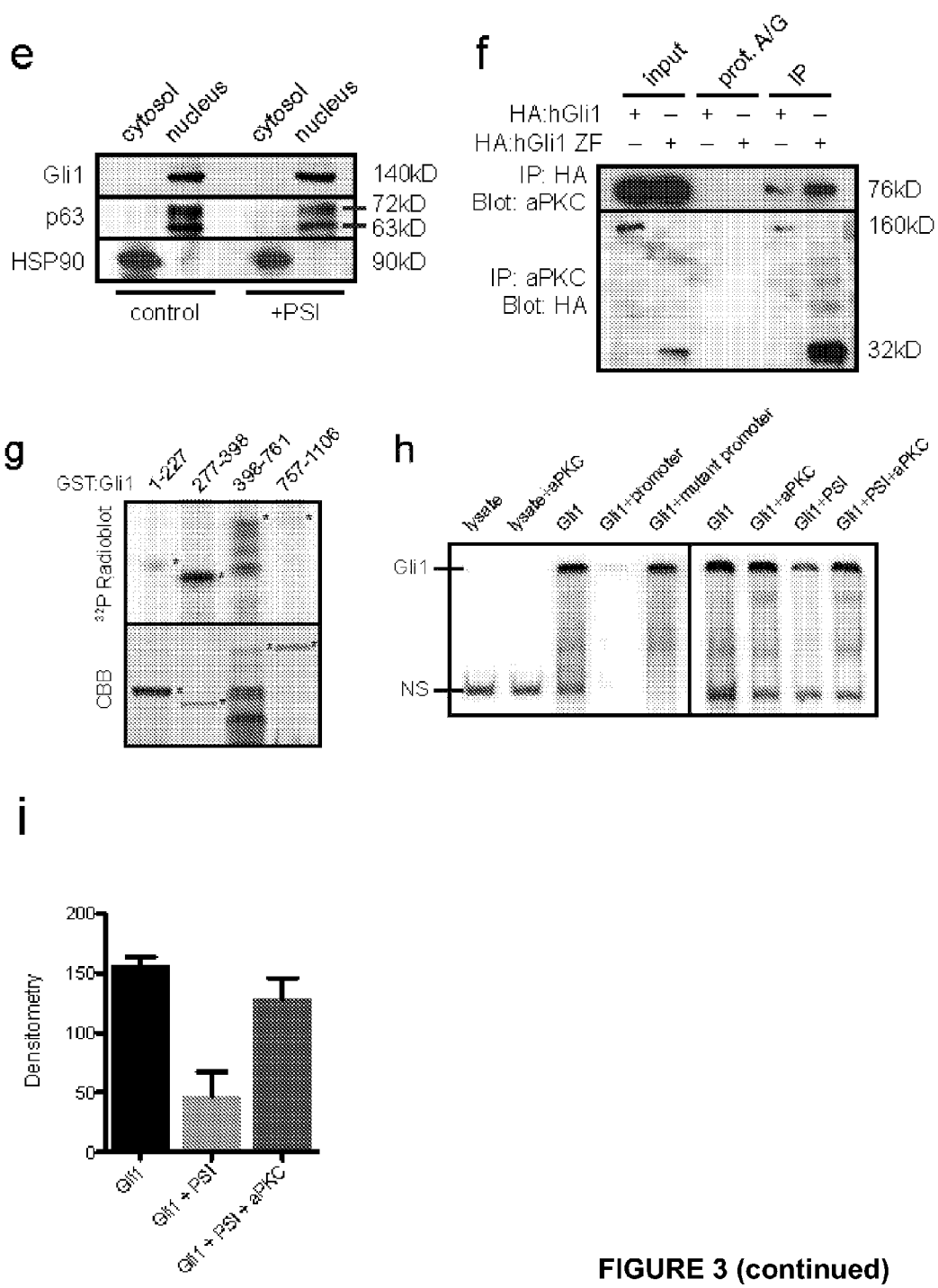
Figure 3:
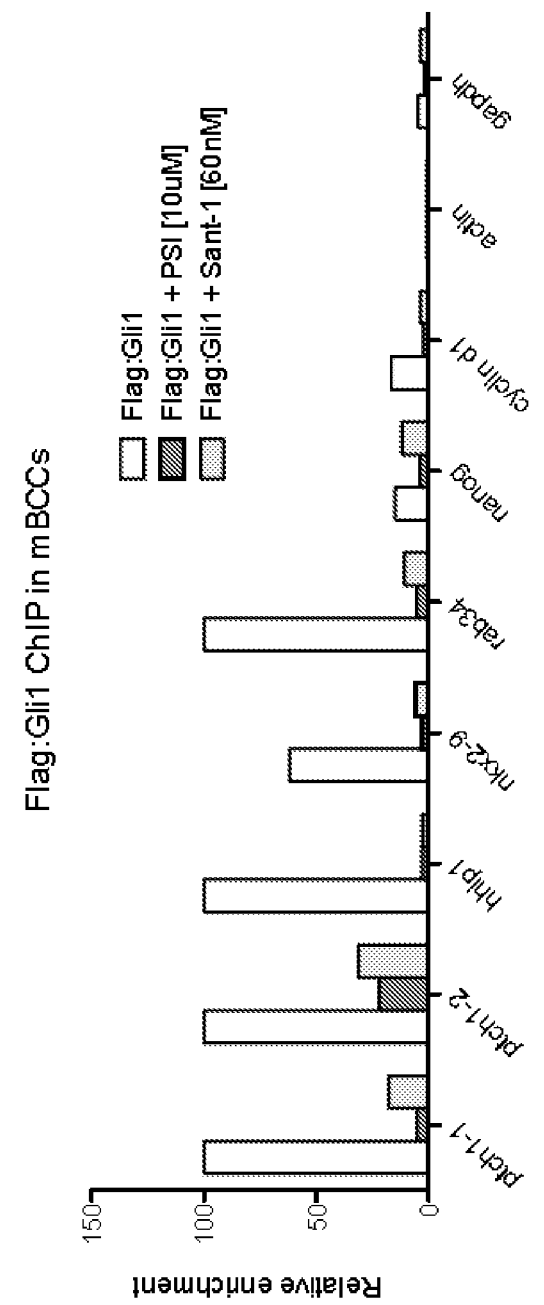
Figure 8:
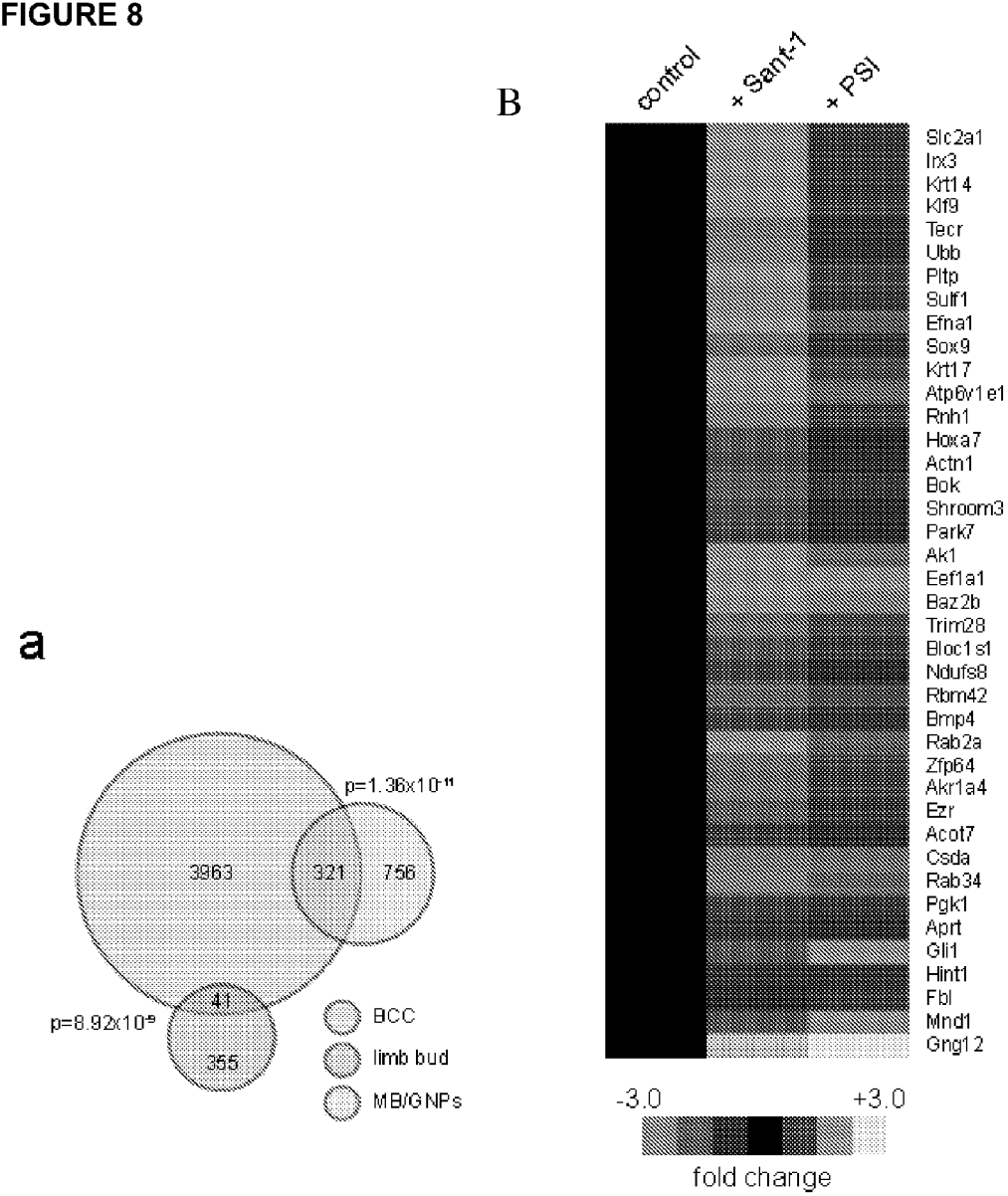
FIG. 8 demonstrates that aPKC inhibition affects Hh target genes. a, Venn diagram and (b) heatmap of commonly altered transcripts in both Sant-1 and PSI-treated samples compared to ChIP-Seq data sets from limb bud and medulloblastoma/GNPs. c, RPKM values and (d) subsequent validated transcript levels of commonly altered transcripts.
Figure 8:
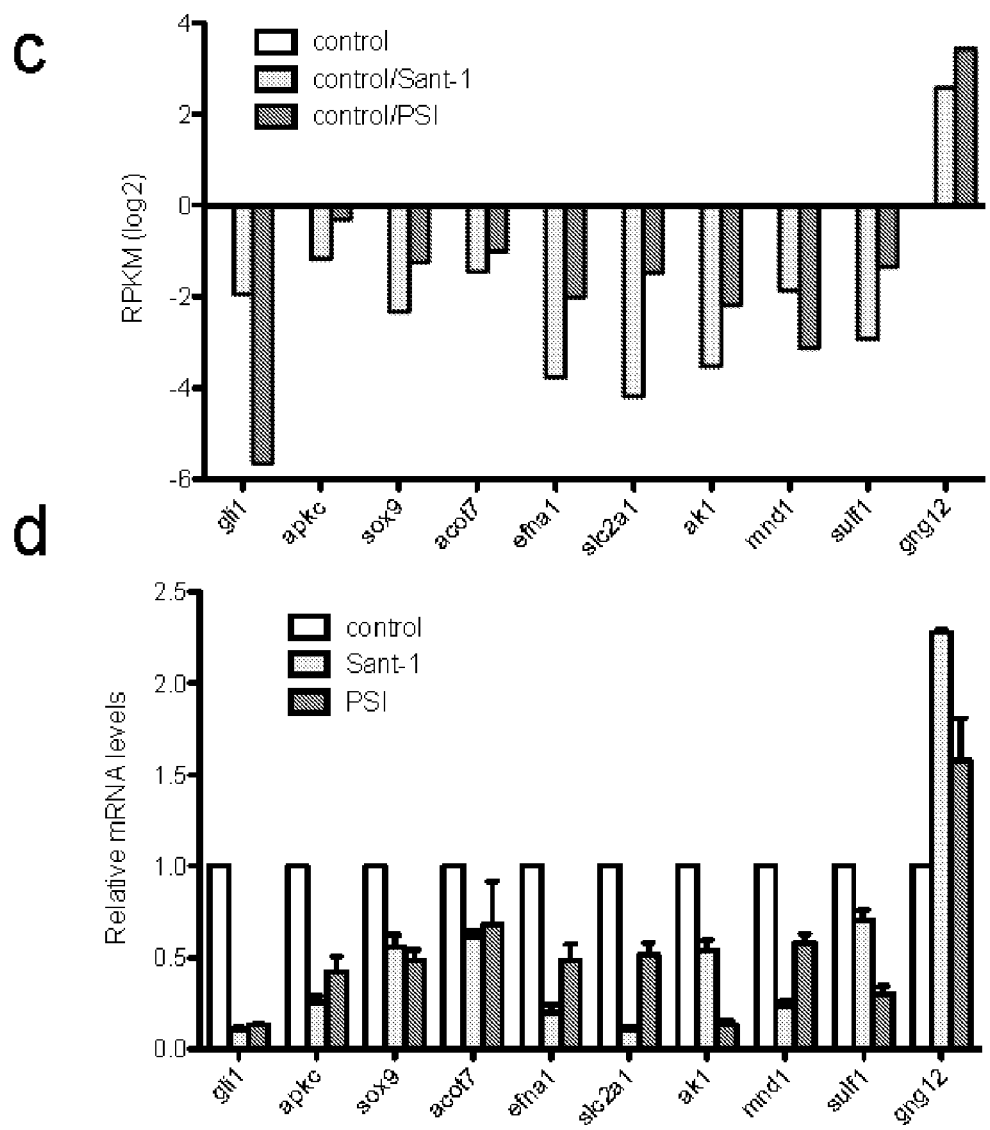

To gain insight into aPKC mechanism of action, we determined whether aPKC-dependent genes in tumors differed from those regulated by Smo. We treated BCC cells with the Smo antagonist Sant-1 or the aPKC inhibitor PSI and performed 3'-end polyadenylated RNA sequencing. Comparison of the data sets showed 5700 Sant-1-dependent or 4762 PZI-dependent transcripts changed two-fold or greater when compared to control (FIG. 3a). 4325 transcripts overlapped between the inhibitor-treated data sets ($p<1.0\times10^{-300}$) with most transcripts downregulated in both sets (FIG. 3b). Gene ontology terms most associated between the commonly changed transcripts include genes involved in cell cycle regulation, protein transport and localization, RNA processing, and cell division (FIG. 3c). Global transcript expression regardless of fold-change showed a strong positive correlation, with a Pearson correlation of 0.495 indicating that inhibiting either Smo or aPKC results in highly similar alterations of the transcriptome. Comparision with previously published Hh-dependent data sets from mouse medulloblastomas/granular neural precursors (GNPs) or developing mouse limb bud (Lee, E. Y. et al. Hedgehog pathway-regulated gene networks in cerebellum development and tumorigenesis. Proceedings of the National Academy of Sciences 107, 9736-9741 (2010); Vokes, S. A., et al. A genome-scale analysis of the cis-regulatory circuitry underlying sonic hedgehog-mediated patterning of the mammalian limb. Genes & Development 22, 2651-2663 (2008)) reveals substantial overlap (FIG. 8a). 321 of the 1077 Gli1 binding sites found in medulloblastomas/GNPs ($p=1.36\times10^{-11}$) and 41 out of 396 ($p=8.92\times10^{-9}$) Gli3 binding sites identified in the developing limb bud overlap with our commonly changed data set. Representative gene expression profiles among the data sets are displayed in a cluster heat map that shows common Gli targets are similarly changed (FIG. 8b). Validation of a subset of transcript expression levels using quantitative RTPCR shows that the RPKM values from our data set closely mirrors actual mRNA levels upon drug treatment (FIG. 8c,d). These results indicate that aPKC and Smo regulate a common set of Hh target genes in BCCs.

Figure 9:
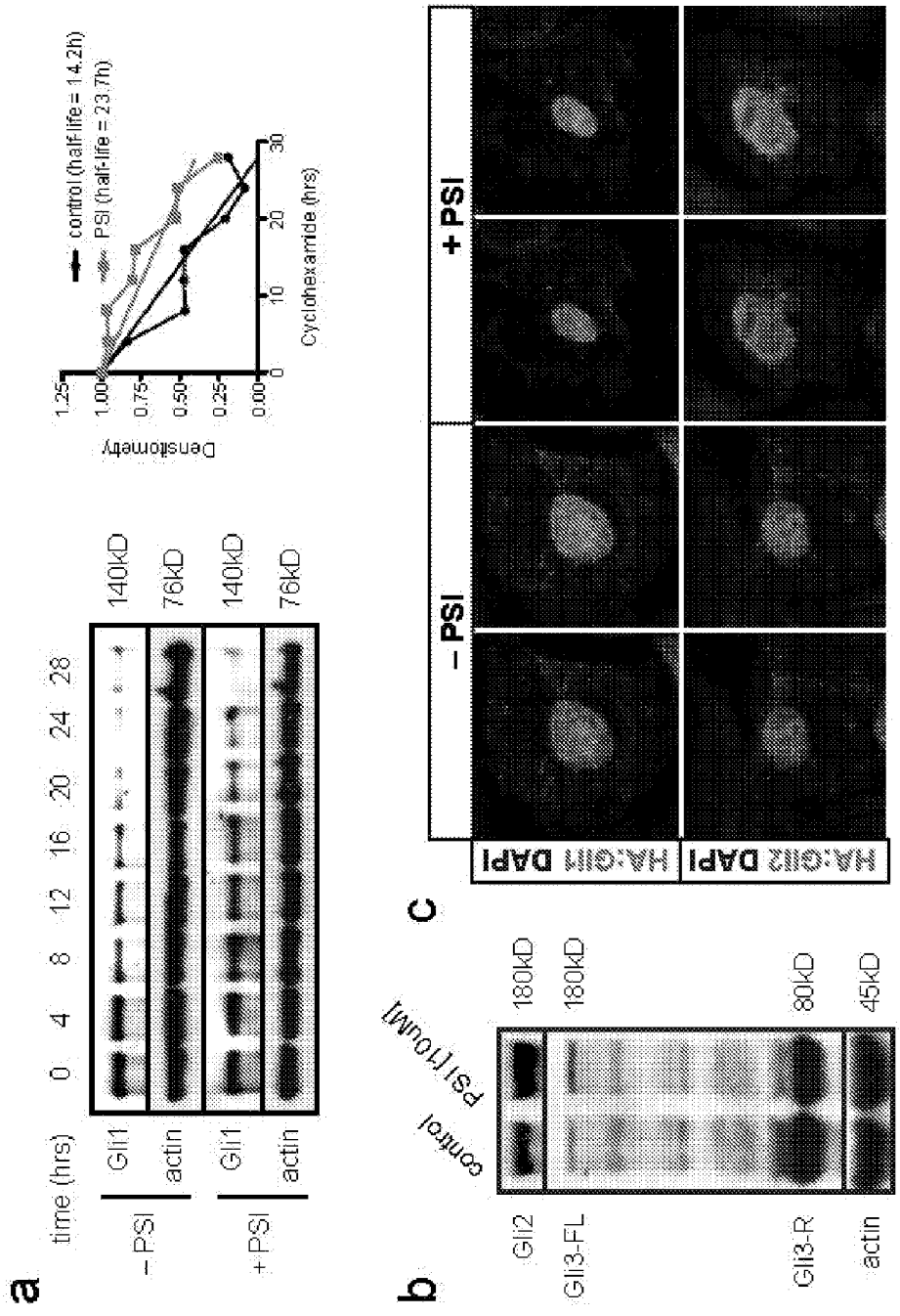
FIG. 9 demonstrates that aPKC does not affect significantly Gli protein stability or processing. a, PSI modestly stabilizes Gli1 protein levels in BCC cells. b, Gli processing is not altered with PSI treatment. c, PSI does not alter nuclear Gli protein localization in BCC cells. d, Gli1 protein has altered electrophoretic mobility with knockdown of aPKC or MIM. e, Densitometry graph of Gli1 protein. f, Over phosphorylation of IVT human Gli1 disrupts DNA binding.
Figure 9:
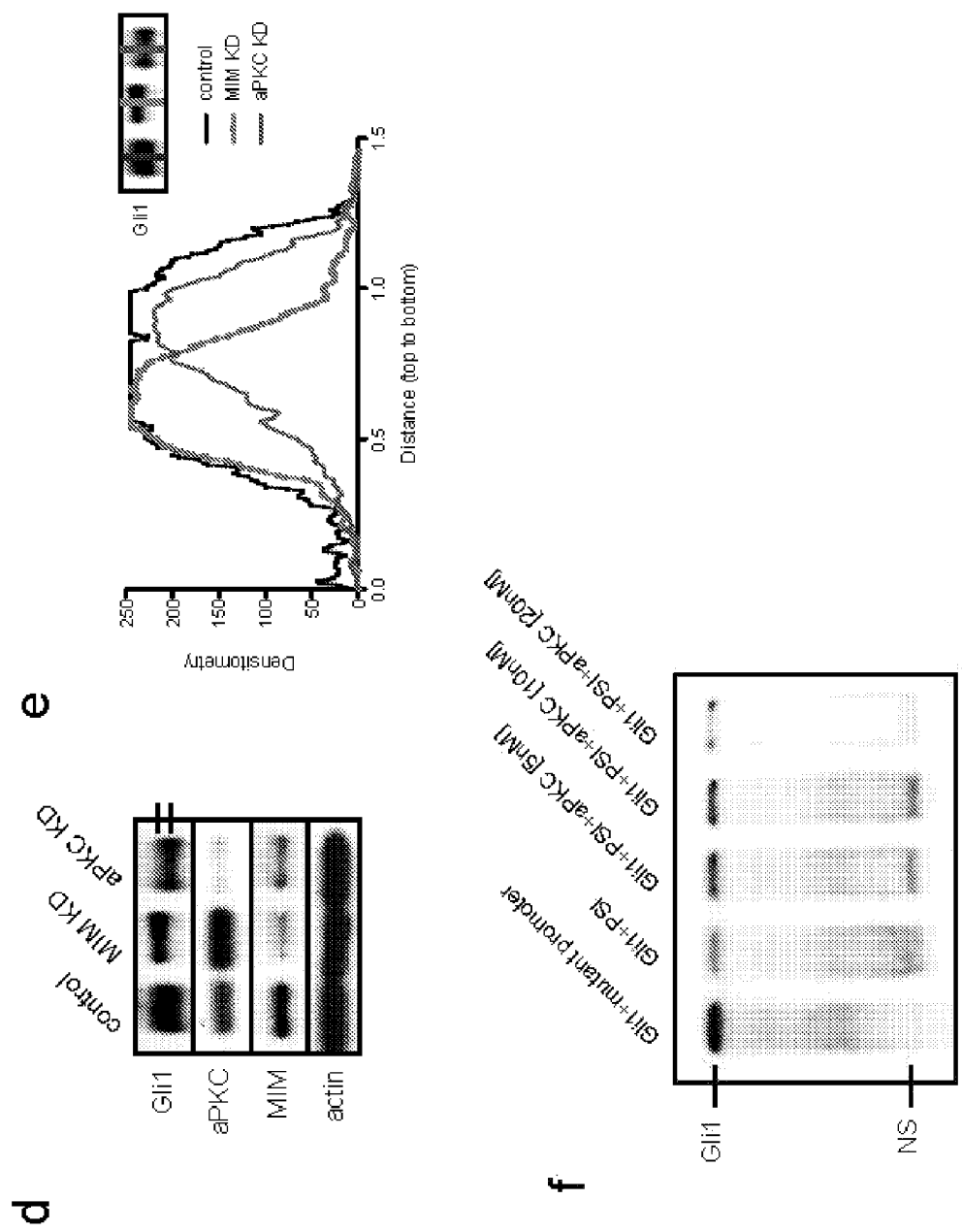

The striking overlap of transcriptional targets suggested that aPKC, as well as Smo, may both regulate the Gli transcription factor. To determine where in the pathway aPKC acts, we asked whether aPKC functions downstream of Smo to regulate Hh signaling. Addition of Smo agonist (SAG) to BCC cells activates gli1 transcription (FIG. 3d). Subthreshold concentrations of cyclopamine that acts on Smo can be outcompeted by SAG-mediated activation. However, PSI-treated cells prevent SAG-induced activation in a dose-dependent manner, indicating aPKC functions downstream of Smo. Gli1 protein levels are mildly reduced in aPKC knockdown cells, so we asked if aPKC affects Gli1 stability. BCC cells treated with cyclohexamide and PSI modestly increased Gli1 stability despite the reduction of Hh signaling (FIG. 9a). In addition, aPKC inhibition does not affect Gli2 or Gli3 processing (FIG. 9b). Moreover, inhibition of aPKC did not affect Gli nuclear localization as endogenous Gli1 levels did not change with addition of inhibitor (FIG. 3e and FIG. 9c) indicating that aPKC affects Gli activity. Intriguingly, loss of aPKC in mouse fibroblasts results in a Gli1 band with slightly smaller molecular weight (FIG. 3f,g). Loss of MIM, despite primary cilia defects that prevent significant activation of the Hh pathway (Bershteyn, M., et al. MIM and cortactin antagonism regulates ciliogenesis and hedgehog signaling. Dev. Cell 19, 270-283 (2010)), have more aPKC protein and a Gli1 band with a slightly larger molecular weight suggesting aPKC may modify Gli1 posttranslationally.

Consistent with the notion of aPKC-dependent alteration of Gli1, aPKC and Gli1 form a complex as recombinant HIS:aPKC and in vitro translated (IVT) human HA:Gli1 or HA:Gli1 zinc finger co-immunoprecipitate, suggesting that aPKC may directly interact and modify Gli1 activity (FIG. 3h). To determine whether aPKC directly phosphorylates Gli1, we performed in vitro kinase reactions with purified aPKC. Indeed, aPKC phosphorylates Gli1 (FIG. 3i), with the majority of the phosphorylation occurring in the zinc finger DNA binding region of Gli1. We asked whether phosphorylated Gli1 affects the mobility of radiolabeled Gli1 target DNA in an electrophoretic mobility assay. IVT human Gli1:V5/HIS efficiently bound to the Gli1 target sequence, whereas aPKC alone did not (FIG. 3j). We treated the in vitro translation mixture with PSI to inhibit endogenous aPKC and saw significantly less Gli1 binding. Addition of recombinant aPKC overcame the effects of PSI to rescue Gli1-dependent DNA binding, indicating Gli1 phosphorylation by aPKC is necessary for maximal DNA binding and Hh signal transduction. The phosphorylation state of Gli1 is sensitive as longer incubation times over phosphorylate Gli1 leading to inhibition of DNA binding (FIG. 9d). To confirm aPKC regulation of Gli binding in vivo, we performed ChIP of Flag:Gli1 in BCC cells using the target genes identified in our 3-Seq data set and other experiments (yokes, S. A. et al. Genomic characterization of Gli-activator targets in sonic hedgehog-mediated neural patterning. Development 134, 1977-1989 (2007); Po, A. et al. Hedgehog controls neural stem cells through p53-independent regulation of Nanog. EMBO J 29, 2646-2658 (2010)). On all Gli1 targets assayed, PSI-treated tumor cells left Gli1 nuclear protein levels unchanged but dramatically reduced the association with chromatin (FIG. 3e,k). Non-Hh target genes were left unchanged by PSI treatment. We conclude that aPKC regulates Hh signaling by phosphorylating and activating Gli1 to increase its affinity for DNA.

Figure 4:
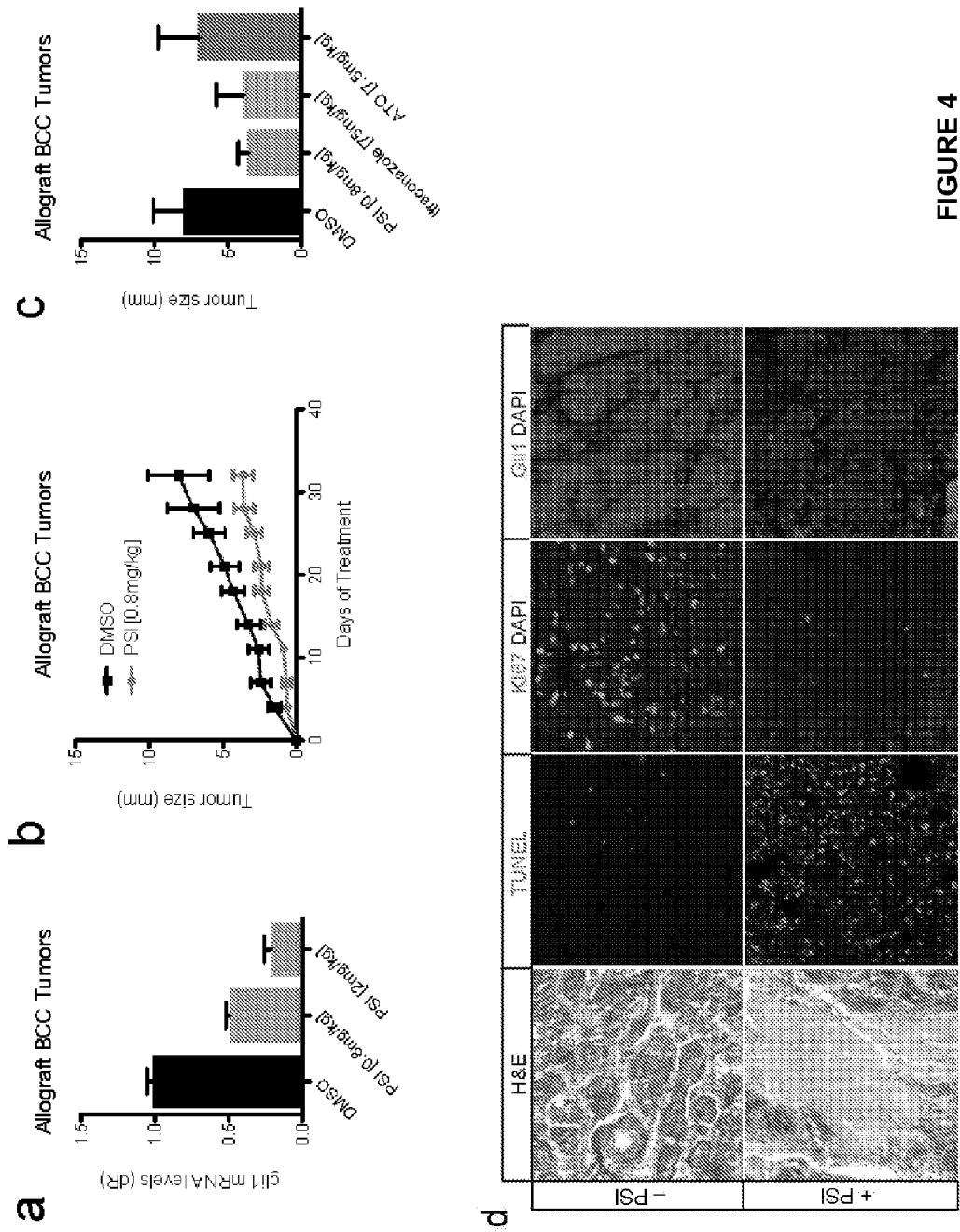
FIG. 4 demonstrates that topical aPKC inhibitor suppresses primary tumor growth. a, Increasing amounts of PSI inhibits Hh signaling in allografted mouse BCC tumors from Ptch1+/−, K14CreER2, p53flox/flox mice. b, Topical treatment of allografted BCC tumors slows tumor growth. c, Intermediate levels of PSI compare favorably to intermediate concentrations of Itraconazole and arsenic trioxide. Error bars, s.e.m. d, BCC tumors lose classical palisades, with an increase in TUNEL-positive cells and a decrease in K167-positive cells and Gli1 stain. e, Five independently derived Smo-resistant BCC cells are sensitive to PSI treatment.
Figure 4:
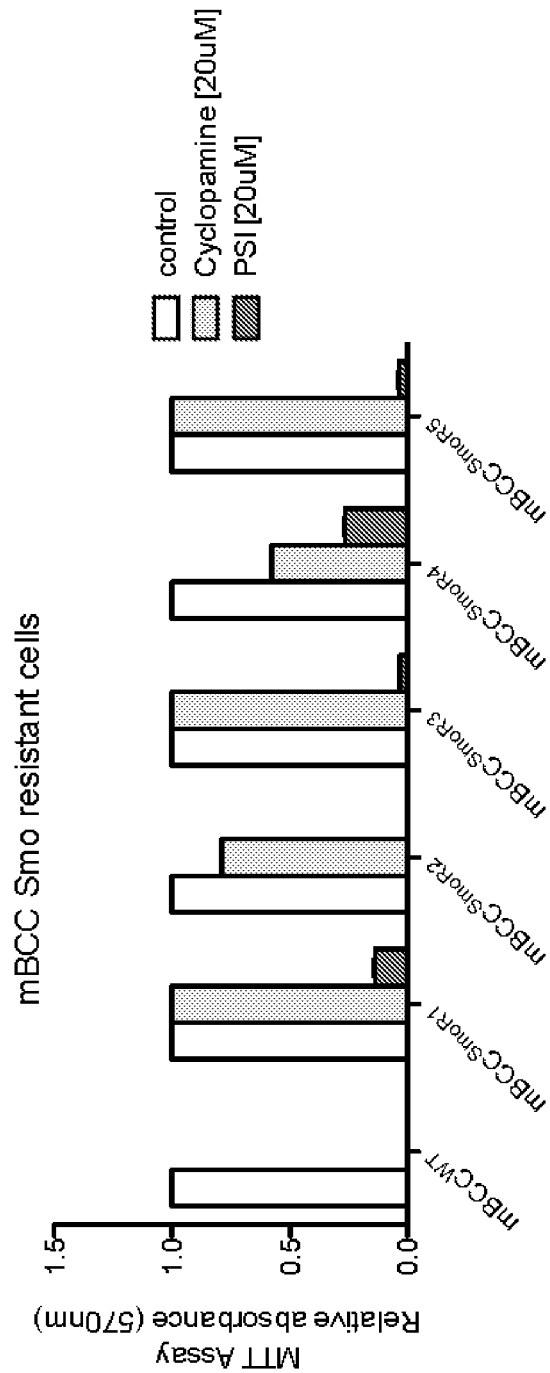
Figure 5:
FIG. 5 provides additional data demonstrating that topical treatment with the psuedosubstrate inhibitor (PSI) of aPKC ("PZI") suppresses Hh signaling in primary BCCs. Shown is the effect of PSI versus DMSO on Gli1 expression levels in primary mBCC tumors that are Ptch$^{-/+}$; p53$^{-/-}$.
Figure 5:
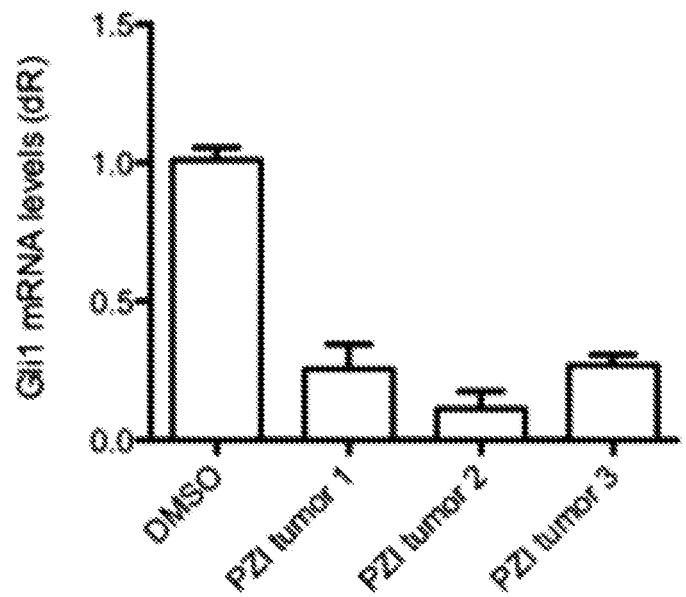
Figure 6:
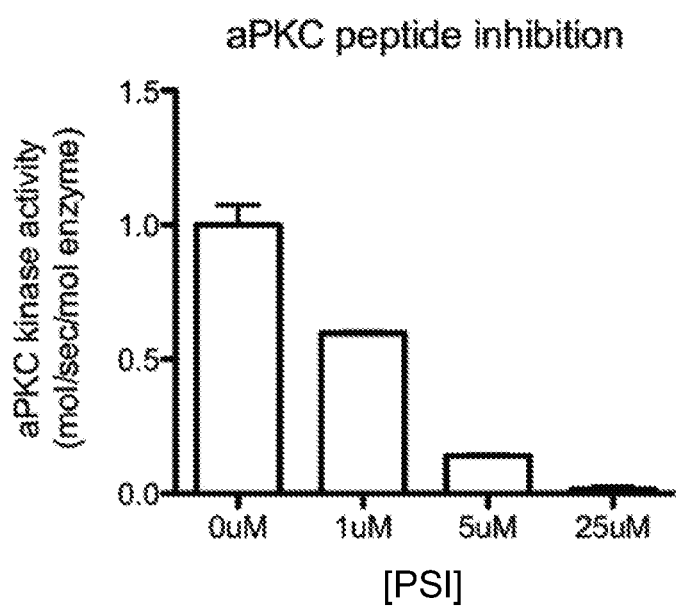
FIG. 6 demonstrates the effect of PSI on aPKC iota kinase activity.

To explore whether aPKC inhibitors can be successfully used as a BCC therapeutic, we topically treated allografted BCC tumors (Wang, G. Y. et al. Establishment of Murine Basal Cell Carcinoma Allografts: A Potential Model for Preclinical Drug Testing and for Molecular Analysis. Journal of Investigative Dermatology (2011)) with aPKC inhibitor. This tumor model faithfully reflects human BCCs and has previously been used to validate Hh pathway inhibitors now in clinical use (Kim, J. et al. Itraconazole, a commonly used antifungal that inhibits Hedgehog pathway activity and cancer growth. Cancer Cell 17, 388-399 (2010)). In allografted BCCs, gli1 mRNA was reduced with increasing concentrations of topical PSI (FIG. 4a). Tumor size was also suppressed with intermediate concentrations of PSI compared to control treatment (FIG. 4b), which compared favorably with treatment of intermediate concentrations of the Smo antagonist itraconazole (Kim, supra) or the Gli2 inhibitor arsenic trioxide (Kim, J., et al. Arsenic antagonizes the Hedgehog pathway by preventing ciliary accumulation and reducing stability of the Gli2 transcriptional effector. Proceedings of the National Academy of Sciences 107, 13432-13437 (2010)) (FIG. 4c). Tumors lost their classical palisade patterning upon PSI treatment and apoptosis dramatically increased as measured by TUNEL staining (FIG. 4d). Cell proliferation was also severely reduced along with Gli1 protein levels. Either topical treatment or high concentrations administered intraperiotoneally, normal skin displayed no adverse effects to PSI treatment except a mild hair phenotype (data not shown) suggesting aPKC treatment is tumor selective.

Because aPKC acts downstream of Smo, we determined whether PSI could inhibit cell growth of Smo-resistant tumors. Following methods to generate resistant lines for other chemotherapeutics like K-ras or B-raf (Little, A. S. et al. Amplification of the driving oncogene, KRAS or BRAF, underpins acquired resistance to MEK1/2 inhibitors in colorectal cancer cells. Science Signaling 4, ra17 (2011)), we generated multiple independent BCC cell lines that were resistant to high levels of Sant-1. We verified Smo resistance by treating the cells with high concentrations of the structurally unrelated cyclopamine and found little effect on cell proliferation (FIG. 4e). Treatment of these lines with PSI dramatically reduced cell proliferation, along with Sant-1 sensitive parental lines. Taken together, these data argue that BCCs become dependent on aPKC to drive Hh activation and tumor growth, and suppression of aPKC activity is sufficient to prevent BCC progression in both Sant-1 sensitive and resistant lines. Our results highlight aPKC inhibition as a viable, tumor-selective alternative to Smo inhibitors to treat Hh-dependent cancers.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method for inhibiting proliferation of a skin cancer cell, the method comprising:
    contacting the skin cancer cell with a pharmaceutical composition comprising an aPKC iota antagonist in an amount effective to inhibit proliferation of the skin cancer cell, wherein the aPKC iota antagonist consists essentially of SEQ ID NO:4,
    wherein activity of aPKC iota is increased in the skin cancer cell as compared to normal skin cell.

2. The method of claim 1, wherein the skin cancer cell is in vitro.

3. The method of claim 1, wherein the method comprises determining Gli activity in the skin cancer cell.

4. The method of claim 3, determining Gli activity comprises measuring amount of phosphorylated Gli.

5. The method of claim 3, wherein determining Gli activity comprises measuring the amount of binding of Gli to a target DNA sequence comprising a sequence to which phosphorylated Gli binds.

6. The method of claim 1, wherein the aPKC iota antagonist consists of SEQ ID NO:4.

7. The method of claim 1, wherein the contacting comprises administering the composition topically.

8. The method of claim 7, wherein the skin cancer cell is in vivo.

9. The method of claim 8, wherein the method comprises determining Gli activity in the skin cancer cell.

10. The method of claim 9, determining Gli activity comprises measuring amount of phosphorylated Gli.

11. The method of claim 9, wherein determining Gli activity comprises measuring the amount of binding of Gli to a target DNA sequence comprising a sequence to which phosphorylated Gli binds.

12. The method of claim 8, wherein the aPKC iota antagonist consists of SEQ ID NO:4.

* * * * *